United States Patent [19]

Diederich et al.

[11] Patent Number: 5,686,459
[45] Date of Patent: Nov. 11, 1997

[54] DIOXOPYRROLO PYRROLE DERIVATIVES

[75] Inventors: Francois Diederich; Ulrike Obst, both of Zurich, Switzerland; Sabine Wallbaum; Lutz Weber, both of Grenzach-Wyhlen, Germany

[73] Assignee: Hoffmann-La Roche Inc., Nutley, N.J.

[21] Appl. No.: 606,811

[22] Filed: Feb. 26, 1996

[30] Foreign Application Priority Data

Feb. 27, 1995 [CH] Switzerland ............... 552/95
Dec. 7, 1995 [CH] Switzerland ............... 3457/95

[51] Int. Cl.⁶ ............... A61K 31/40; A61K 31/495; C07D 403/04; C07D 487/06
[52] U.S. Cl. ............... 514/260; 514/259; 514/292; 514/299; 514/366; 514/411; 514/421; 544/284; 546/81; 546/112; 548/151; 548/453
[58] Field of Search ............... 514/260, 259, 514/292, 299, 366, 411, 421; 544/284; 546/81, 112; 548/151, 453

[56] References Cited

U.S. PATENT DOCUMENTS 4,912,107  3/1990  Kleinschroth et al. ............... 514/232.5

FOREIGN PATENT DOCUMENTS

| 529 152 | 10/1972 | Czech Rep. . |
| 544 763 | 1/1974 | Czech Rep. . |
| 546 776 | 3/1974 | Czech Rep. . |
| 0362 695 | 4/1990 | European Pat. Off. . |
| WO-A-94 14438 | 7/1994 | WIPO . |

OTHER PUBLICATIONS

Aly, et al. Non-Decarboxylative 1,3-Dipolar Cycloadditions of Imines of α-Amino Acids as a Route to Proline Derivatives, Tetrahedron, vol. 50, No. 10, pp. 3159-3168 (1994).

Grigg, et al., The Decarboxylative Route to Azomethine Ylides. Stereochemistry of 1,3-Dipole Formation, J. Chem. Soc., Chem. Commun. pp. 47-49 (1987).

Grigg, et al. X=Y-ZH Systems as Potential 1,3-Dipoles, Part 11. Stereochemistry of 1,3-Dipoles Generated by the Decarboxylative Route to Azomethine Ylides, J. Chem. Soc. Perkin Trans. I pp. 2693-2701 (1988).

Grigg, et al., The Decarboxylative Route to Azomethine Ylides. Mechanism of 1,3-Dipole Formation, J. Chem. Soc. Chem. Commun. pp. 49-51 (1987).

*Primary Examiner*—Joseph McKane
*Attorney, Agent, or Firm*—George W. Johnston; Patricia S. Rocha-Tramaloni; Raina Semionow

[57] ABSTRACT

Novel dioxopyrrolo-pyrrole derivatives of the formula

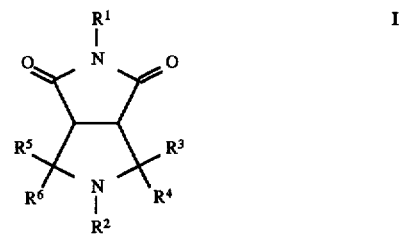

as well as hydrates or solvates thereof, which inhibit thrombin-induced or Factor Xa-induced platelet aggregation and fibrinogen clotting in blood plasma. The derivatives can be manufactured from the corresponding maleimides which are N-substituted by α-amino carboxylic acids of the formula $HN(R^2)CH(R^4)COOH$, or functional derivatives thereof; and ketones or aldehydes of the formula $R^5C(O)R^6$.

31 Claims, No Drawings

DIOXOPYRROLO PYRROLE DERIVATIVES

The present invention is directed to novel dioxopyrrolo-pyrrole derivatives. In particular, the present invention is directed to octahydro-1,3-dioxo-pyrrolo[3,4-c]pyrrole derivatives of the formula

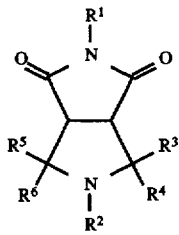

wherein
- $R^1$ is selected from the group consisting of H, lower alkyl, aryl, heteroaryl, cycloalkyl and lower-alkyl which is substituted with a group $R^{10}$ and optionally a group $R^{11}$ or with a group $R^{11}$ and optionally a group $R^{10}$;
- $R^2$ is selected from the group consisting of lower-alkanoyl, H, lower-alkyl, aryl, heteroaryl, cycloalkyl and lower-alkyl which is substituted with a group $R^{10}$ and optionally a group $R^{11}$ or with a group $R^{11}$ and optionally a group $R^{10}$;
- $R^{10}$ is $CONH_2$ or COO-lower-alkyl;
- $R^{11}$ is aryl, heteroaryl or cycloalkyl;
- $R^3$ is selected from the group consisting of H, COOH, $CONH_2$, COO-lower-alkyl, CONH-lower-alkyl and CON(lower-alkyl)$_2$; and
- $R^4$, $R^5$ and $R^6$ are each independently selected from the group consisting of H, lower alkyl, aryl, aralkyl or cycloalkyl, or
- $R^4$ and optionally $R^5$ or $R^6$ are a group $R^{40}$, or
- $R^5$ or $R^6$ and optionally $R^4$ are a group $R^{40}$;
- $R^{40}$ is heteroaryl, or lower-alkyl substituted with OH, $SO_2H$, $SO_3H$, guanidino, aryl-lower-alkoxy or lower-alkyl-(O or S); or
- $R^2$ and $R^4$ together form a group G, wherein G is a tri- or tetramethylene group $(CH_2)_3$ or $(CH_2)_4$ wherein one methylene group may be replaced by S, SO or $SO_2$, or may be substituted with OH, lower-alkyl, lower-alkenyl or carboxy-lower-alkyl, or wherein one methylene group may be substituted with lower-alkenyl and another methylene group may be substituted with carboxy-lower-alkyl;

with the proviso that at least one of $R^1$, $R^2$, $R^4$, $R^5$ and $R^6$ is a group substituted with amino, amidino, guanidino or N-hydroxyamidino, and hydrates or solvates and physiologically usable salts thereof.

The invention is also concerned with a process for the manufacture of the above compounds, pharmaceutical preparations which contain such compounds, as well as the use of these compounds in the production of pharmaceutical preparations.

Examples of physiologically usable salts of the compounds of Formula I are salts with physiologically compatible mineral acids, including, for example, hydrochloric acid, sulfuric acid, sulfurous acid or phosphoric acid; or with organic acids, including, for example, methanesulfonic acid, p-toluenesulfonic acid, acetic acid, trifluoroacetic acid, citric acid, fumaric acid, maleic acid, tartaric acid, succinic acid or salicylic acid. The compounds of Formula I having an acidic group such as a carboxy group can also form salts with physiologically compatible bases. Examples of such salts are alkali metal, alkaline earth metal, ammonium and alkylammonium salts such as the Na, K, Ca or tetramethylammonium salt. The compounds of Formula I can also be present in the form of zwitterions.

The compounds of Formula I can be solvated, especially hydrated. The hydration can be effected in the course of the manufacturing process or can occur gradually as a consequence of hygroscopic properties of an initially anhydrous compound of Formula I.

The compounds of Formula I contain at least two asymmetric C atoms and can therefore be present as a mixture of diastereomers, as a mixture of enantiomers or as the optically pure compound.

In the scope of the present invention "lower" denotes a straight-chain or branched group containing up to 6 C atoms. Preferred lower-alkyl or lower-alkanoyl groups contain up to 4 C atoms. Examples of these are methyl, isopropyl, butyl, isobutyl, sec-butyl and tert.-butyl and, respectively, acetyl. "Aryl" alone or in combination denotes groups such as phenyl which can be substituted by, for example, amidino, guanidino, hydroxyamidino, nitro, amino or methylenedioxy. "Aralkyl" denotes aryl bonded via lower-alkylene, for example, benzyl or phenethyl substituted in the phenyl ring. "Cycloalkyl" denotes saturated groups with 3 to 7 C atoms such as cyclohexyl. "Heteroaryl" denotes 5- to 10-membered aromatic groups which, for example, can comprise two rings, which contains one (or more) N atom(s) and which can be substituted by, for example, one or more $NH_2$ groups. Examples of such groups are quinazolinyl and 2,4-diaminoquinazolin-6 or 7-yl. Groups substituted with amino, guanidino or N-hydroxyamidino may include quinazolinyl substituted by amino and (amino, amidino, guanidino or N-hydroxyamidino)-(lower-alkyl, phenyl or benzyl).

The compounds of Formula I include compounds in which $R^1$ to $R^6$ have the above significances, wherein $R^2$ is lower alkanoyl, H, lower alkyl, aryl, heteroaryl, cycloalkyl or lower-alkyl which is substituted with a group $R^{10}$ and optionally a group $R^{11}$ or with a group $R^{11}$ and optionally a group $R^{10}$. In these compounds, $R^2$ is preferably selected from the group consisting of H, lower-alkyl, lower-alkanoyl or lower-alkyl substituted by $CONH_2$; and most preferably selected from H, methyl, carbamoylethyl or acetyl.

The compounds of Formula I include those wherein $R^2$ and $R^4$ together form a group G as defined above and, thus, form compounds having the formula

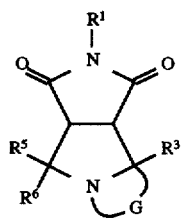

wherein G is a tri- or tetramethylene group in which a) one of the methylene groups may be replaced by S, SO or $SO_2$ or may be substituted by OH, lower-alkyl, lower-alkenyl or carboxy-lower-alkyl; or b) one of the methylene groups may be substituted with lower alkenyl and another methylene group may be substituted by lower-alkyl-COOH, provided that at least one of $R^1$, $R^4$, $R^5$ and $R^6$ is a group substituted with amino, amidino, guanidino or N-hydroxyamidino; as well as hydrates or solvates and physiologically usable salts thereof.

Examples of compounds of Formula I' include compounds wherein G is a group $(CH_2)_3$ or $(CH_2)_4$, in which one of the CH$_2$ groups may be replaced by S, CH-lower-alkyl or CHOH; or one of the CH$_2$ groups may be substituted by lower-alkenyl and another may be substituted by lower-alkyl-COOH. Preferred compounds of Formula I' include compounds wherein G is selected from the group consisting of (CH$_2$)$_3$, (CH$_2$)$_4$, CH(CH$_3$)CH$_2$CH$_2$, CH$_2$SCH$_2$, CH$_2$S(O)$_2$CH$_2$, CH$_2$CH(OH)CH$_2$ and CH(CH$_2$COOH)CH (isopropylene)CH$_2$.

Compounds of Formula I or I' are preferred in which R$^1$ is H, lower-alkyl, aryl or lower-alkyl substituted by a group R$^{10}$ or R$^{110}$ and optionally by a group R$^{110}$ or R$^{10}$, respectively, in which R$^{10}$ is CONH$_2$ or COO-lower-alkyl and R$^{110}$ is aryl or cycloalkyl; especially preferred compounds are those in which R$^1$ is H, CH$_3$, butyl, phenyl, benzyl, phenethyl, cyclohexylmethyl or benzyl substituted by nitro, amino or methylenedioxy, especially benzo[1,3]dioxol-5-ylmethyl.

Preferred compounds of Formula I' are those in which R$^1$ is CH$_3$, butyl, phenyl, benzyl, benzyl substituted by methylenedioxy cyclohexylmethyl, lower-alkyl substituted by CONH$_2$ or COO-lower-alkyl, and aryl; especially preferred compounds are benzo[1,3]dioxol-5-ylmethyl or 1-(carbamoyl or carbomethoxy)-2-phenylethyl, especially in which R$^3$ is H or COOH, especially in which R$^5$ is H and R$^6$ is aryl or heteroaryl, especially amidinophenyl, guanidinophenyl or diaminoquinazoline.

Preferred compounds of Formula I are, further, those in which R$^3$ is H, COOH or CONH$_2$, especially in which R$^4$ is H, lower-alkyl, aryl, aralkyl or lower-alkyl substituted by OH, SO$_2$H, guanidino, aralkoxy or lower-alkylthio, especially in which R$^4$ is H, methyl, isopropyl, isobutyl, 2-butyl, tert.-butyl, phenyl, benzyl, CH$_2$OH, CH$_2$SO$_2$H, guanidinopropyl, benzyloxymethyl or (CH$_2$)$_2$SCH$_3$.

Preferred compounds of Formula I are also those in which R$^5$ and R$^6$ are each independently H, lower-alkyl, aryl or aralkyl, especially H, methyl, tert.-butyl, phenyl, phenethyl, amidinophenyl or hydroxyamidinophenyl.

Examples of preferred compounds of Formulae I and, respectively, I' are (1RS,3SR,3aRS,6aSR)-4-(5-benzyl-2,3-dimethyl-4,6-dioxo-octahydro-pyrrolo[3,4-c]pyrrol-1-yl)-benzimidamide; and, respectively, (3aRS,4SR,8aRS,8bSR)-4-(2-benzyl-1,3-dioxo-decahydro-pyrrolo[3,4-a]pyrrolizin-4-yl)-benzimidamide;

(3aRS,4SR,8aRS,8bSR)-4-[2-(benzo[1,3]dioxol-5-ylmethyl)-1,3-dioxo-decahydro-pyrrolo[3,4-a]pyrrolizin-4-yl]-benzimidamide;

(3aRS,4SR,8aRS,8bSR)-4-(2-cyclohexylmethyl-1,3-dioxo-decahydro-pyrrolo[3,4-a]pyrrolizin-4-yl)-benzimidamide;

(5RS,5aSR,8aRS,8bRS)-4-[7-(benzo[1,3]dioxol-5-ylmethyl)-6,8-dioxo-octahydro-pyrrolo[3',4':3,4]pyrrolo[1,2-c]thiazol-5-yl]-benzimidamide;

(3aR,4S,7S,8aR,8bS)-4-(2-benzyl-7-hydroxy-1,3-dioxo-decahydro-pyrrolo[3,4-a]pyrrolizin-4-yl)-benzimidamide; and (3aRS,4SR,8aRS,8bSR)-N-[4-(2-butyl-1,3-dioxo-decahydro-pyrrolo[3,4-a]pyrrolizin-4-yl)-phenyl]-guanidine.

Further examples of preferred compounds of Formula I are:

(1RS,3RS,3aSR,6aRS)-1-(Benzyloxy-methyl)-3-(4-carbamimidoyl-phenyl)-5-(4-nitro-benzyl)-4,6-dioxo-octahydro-pyrrolo-[3,4-c]pyrrole-1-carboxylic acid; and (1RS,3RS,3aSR,6aRS)-5-(4-amino-benzyl)-1-(benzyloxy-methyl)-3-(4-carbamimidoyl-phenyl)-4,6-dioxo-octahydro-pyrrolo[3,4-c]-pyrrole-1-carboxylic acid.

Further examples of compounds of Formulae I and, respectively, I' are:

(1RS,3SR,3aRS,6aSR)-5-Benzyl-1-(3-guanidino-propyl)-4,6-dioxo-octahydro-3-phenyl-pyrrolo[3,4-c]pyrrole-1-carboxylic acid;

(1RS,3aSR,6aRS)-4-(5-benzyl-2,3,3-trimethyl-4,6-dioxo-octahydro-pyrrolo[3,4-c]pyrrol-1-ylmethyl)-benzimidamide;

(3aRS,4RS,6aSR)-4-[4-(amino-hydroxyimino-methyl)-benzyl]-2-benzyl-5,6,6-trimethyl-tetrahydro-pyrrolo[3,4-c]pyrrole-1,3-dione;

(1RS,3SR,3aRS,6aSR)-4-(5-benzyl-3-methyl-4,6-dioxo-octahydro-pyrrolo[3,4-c]pyrrol-1-yl)-benzimidamide;

(1RS,3SR,3aRS,6aSR)-4-(2-acetyl-5-benzyl-3-methyl-4,6-dioxo-octahydro-pyrrolo[3,4-c]pyrrol-1-yl)-benzimidamide;

(1RS,3SR,3aRS,6aSR)-4-(5-butyl-2,3-dimethyl-4,6-dioxo-octahydro-pyrrolo[3,4-c]pyrrol-1-yl)-benzimidamide;

(1RS,3SR,3aRS,6aSR)-4-(2-acetyl-5-butyl-3-methyl-4,6-dioxo-octahydro-pyrrolo[3,4-c]pyrrol-1-yl)-benzimidamide;

(3aRS,4SR,6RS,6aSR)-4-[4-(amino-hydroxyimino-methyl)-phenyl]-2-benzyl-5,6-dimethyl-tetrahydro-pyrrolo[3,4-c]pyrrole-1,3-dione;

(1RS,3SR,3aRS,6aSR)-4-(5-butyl-3-methyl-4,6-dioxo-octahydro-pyrrolo[3,4-c]pyrrol-1-yl)-benzimidamide;

(1RS,3SR,3aRS,6aSR)-4-(5-benzyl-3-isobutyl-4,6-dioxo-octahydro-pyrrolo[3,4-c]pyrrol-1-yl)-benzimidamide;

(1RS,3SR,3aRS,6aSR)-4-(5-benzyl-3-isobutyl-2-methyl-4,6-dioxo-octahydro-pyrrolo[3,4-c]pyrrol-1-yl)-benzimidamide;

(1RS,3RS,3aSR,6aRS)-[5-(benzo[1,3]dioxol-5-ylmethyl)-3-(4-carbamimidoyl-phenyl) -4,6-dioxo-octahydro-pyrrolo[3,4-c]pyrrol-1-yl]-methanesulfonic acid;

(1RS,3RS,3aSR,6aRS)-[5-(benzo[1,3]dioxol-5-ylmethyl)-3-(4-carbamimidoyl-phenyl)-4,6-dioxo-octahydro-pyrrolo[3,4-c]pyrrol-1-yl]-methanesulfonic acid;

(1RS,3SR,3aRS,6aSR)-3-(4-carbamimidoyl-phenyl)-1-(2-methyl-sulfanyl-ethyl)-4,6-dioxo-5-phenyl-octahydro-pyrrolo[3,4-c]pyrrole-1-carboxylic acid;

(1RS,3SR,3aRS,6aSR)-4-[5-(benzo[1,3]dioxol-5-ylmethyl)-3-hydroxymethyl-4,6-dioxo-octahydro-pyrrolo[3,4-c]pyrrol-1-yl]-benzimidamide;

(1RS,3RS,3aSR,6aRS)-4-[5-(benzo[1,3]dioxol-5-ylmethyl)-3-hydroxymethyl-4,6-dioxo-octahydro-pyrrolo[3,4-c]pyrrol-1-yl]-benzimidamide;

3-tert.butyl-1-(3-guanidino-propyl)-4,6-dioxo-octahydro-pyrrolo[3,4-c]pyrrole-1-carboxamide;

3-phenyl-1-(3-guanidino-propyl)-4,6-dioxo-octahydro-pyrrolo-[3,4-c]pyrrole-1-carboxamide;

3-(2-phenyl-ethyl)-1-(3-guanidino-propyl)-4,6-dioxo-octahydro-pyrrolo[3,4-c]pyrrole-1-carboxamide;

5-methyl-3-(2-phenyl-ethyl)-1-(3-guanidino-propyl)-4,6-dioxo-octahydro-pyrrolo[3,4-c]pyrrole-1-carboxamide;

5-butyl-3-(2-phenyl-ethyl)-1-(3-guanidino-propyl)-4,6-dioxo-octahydro-pyrrolo[3,4-c]pyrrole-1-carboxamide;

5-cyclohexylmethyl-3-(2-phenyl-ethyl)-1-(3-guanidino-propyl)-4,6-dioxo-octahydro-pyrrolo[3,4-c]pyrrole-1-carboxamide;

5-benzyl-3-(2-phenyl-ethyl)-1-(3-guanidino-propyl)-4,6-dioxo-octahydro-pyrrolo[3,4-c]pyrrole-1-carboxamide;

5-phenyl-3-(2-phenyl-ethyl)-1-(3-guanidino-propyl)-4,6-dioxo-octahydro-pyrrolo[3,4-c]pyrrole-1-carboxamide;

5-butyl-3,3-diphenyl-1-(3-guanidino-propyl)-4,6-dioxo-octahydro-pyrrolo[3,4-c]pyrrole-1-carboxamide;

5-butyl-3-phenyl-1-(3-guanidino-propyl)-4,6-dioxo-octahydro-pyrrolo[3,4-c]pyrrole-1-carboxamide;

5-cyclohexylmethyl-3-phenyl-1-(3-guanidino-propyl)-4,6-dioxo-octahydro-pyrrolo[3,4-c]pyrrole-1-carboxamide;

5-benzyl-3-phenyl-1-(3-guanidino-propyl)-4,6-dioxo-octahydro-pyrrolo[3,4-c]pyrrole-1-carboxamide;

3,5-diphenyl-1-(3-guanidino-propyl)-4,6-dioxo-octahydro-pyrrolo[3,4-c]pyrrole-1-carboxamide;

5-butyl-3-tert.butyl-1-(3-guanidino-propyl)-4,6-dioxo-octahydro-pyrrolo[3,4-c]pyrrole-1-carboxamide;

5-butyl-1-(3-guanidino-propyl)-4,6-dioxo-octahydro-pyrrolo-[3,4-c]pyrrole-1-carboxamide;

1-(3-guanidino-propyl)-4,6-dioxo-octahydro-5-phenyl-pyrrolo[3,4-c]pyrrole-1-carboxamide;

5-methyl-3-(4-carbamimidoyl-phenyl)-4,6-dioxo-octahydro-pyrrolo[3,4-c]pyrrole-1-carboxylic acid;

1,5-dimethyl-3-(4-carbamimidoyl-phenyl)-4,6-dioxo-octahydro-pyrrolo[3,4-c]pyrrole-1-carboxylic acid;

5-methyl-1-(2-propyl)-3-(4-carbamimidoyl-phenyl)-4,6-dioxo-octahydro-pyrrolo[3,4-c]pyrrole-1-carboxylic acid;

1-(2-butyl)-5-methyl-3-(4-carbamimidoyl-phenyl)-4,6-dioxo-octahydro-pyrrolo[3,4-c]pyrrole-1-carboxylic acid;

5-methyl-1-(2-methylsulfanyl-ethyl)-3-(4-carbamimidoyl-phenyl)-4,6-dioxo-octahydro-pyrrolo[3,4-c]pyrrole-1-carboxylic acid;

5-butyl-3-(4-carbamimidoyl-phenyl)-4,6-dioxo-octahydro-pyrrolo[3,4-c]pyrrole-1-carboxylic acid;

5-butyl-1-methyl-3-(4-carbamimidoyl-phenyl)-4,6-dioxo-octahydro-pyrrolo[3,4-c]pyrrole-1-carboxylic acid;

5-butyl-1-(2-propyl)-3-(4-carbamimidoyl-phenyl)-4,6-dioxo-octahydro-pyrrolo[3,4-c]pyrrole-1-carboxylic acid;

5-butyl-1-(2-butyl)-3-(4-carbamimidoyl-phenyl)-4,6-dioxo-octahydro-pyrrolo[3,4-c]pyrrole-1-carboxylic acid;

5-butyl-1-(2-methylsulfanyl-ethyl)-3-(4-carbamimidoyl-phenyl)-4,6-dioxo-octahydro-pyrrolo[3,4-c]pyrrole-1-carboxylic acid;

5-cyclohexylmethyl-3-(4-carbamimidoyl-phenyl)-4,6-dioxo-octahydro-pyrrolo[3,4-c]pyrrole-1-carboxylic acid;

5-cyclohexylmethyl-1-(2-propyl)-3-(4-carbamimidoyl-phenyl)-4,6-dioxo-octahydro-pyrrolo[3,4-c]pyrrole-1-carboxylic acid;

1-(2-butyl)-5-cyclohexylmethyl-3-(4-carbamimidoyl-phenyl)-4,6-dioxo-octahydro-pyrrolo[3,4-c]pyrrole-1-carboxylic acid;

5-cyclohexylmethyl-1-(2-methylsulfanyl-ethyl)-3-(4-carbamimidoyl-phenyl)-4,6-dioxo-octahydro-pyrrolo[3,4-c]pyrrole-1-carboxylic acid;

5-phenyl-3-(4-carbamimidoyl-phenyl)-4,6-dioxo-octahydro-pyrrolo[3,4-c]pyrrole-1-carboxylic acid;

1-methyl-5-phenyl-3-(4-carbamimidoyl-phenyl)-4,6-dioxo-octahydro-pyrrolo[3,4-c]pyrrole-1-carboxylic acid;

5-phenyl-1-(2-propyl)-3-(4-carbamimidoyl-phenyl)-4,6-dioxo-octahydro-pyrrolo[3,4-c]pyrrole-1-carboxylic acid;

1-(2-butyl)-5-phenyl-3-(4-carbamimidoyl-phenyl)-4,6-dioxo-octahydro-pyrrolo[3,4-c]pyrrole-1-carboxylic acid;

1-(2-methylsulfanyl-ethyl)-5-phenyl-3-(4-carbamimidoyl-phenyl)-4,6-dioxo-octahydro-pyrrolo[3,4-c]pyrrole-1-carboxylic acid;

5-benzyl-3-(4-carbamimidoyl-phenyl)-4,6-dioxo-octahydro-pyrrolo[3,4-c]pyrrole-1-carboxylic acid;

5-benzyl-1-methyl-3-(4-carbamimidoyl-phenyl)-4,6-dioxo-octahydro-pyrrolo[3,4-c]pyrrole-1-carboxylic acid;

5-benzyl-1-(2-propyl)-3-(4-carbamimidoyl-phenyl)-4,6-dioxo-octahydro-pyrrolo[3,4-c]pyrrole-1-carboxylic acid;

5-benzyl-1-(2-butyl)-3-(4-carbamimidoyl-phenyl)-4,6-dioxo-octahydro-pyrrolo[3,4-c]pyrrole-1-carboxylic acid;

5-benzyl-3-(4-carbamimidoyl-phenyl)-1-(2-methylsulfanyl-ethyl)-4,6-dioxo-octahydro-pyrrolo[3,4-c]pyrrole-1-carboxylic acid;

5-methyl-1-(4-carbamimidoyl-phenyl)-2-(2-carbamoyl-ethyl)-4,6-dioxo-octahydro-pyrrolo[3,4-c]pyrrole-3-carboxylic acid;

3,5-dimethyl-1-(4-carbamimidoyl-phenyl)-2-(2-carbamoyl-ethyl)-4,6-dioxo-octahydro-pyrrolo[3,4-c]pyrrole-3-carboxylic acid;

5-methyl-3-(prop-2-yl)-1-(4-carbamimidoyl-phenyl)-2-(2-carbamoyl-ethyl)-4,6-dioxo-octahydro-pyrrolo[3,4-c]pyrrole-1-carboxylic acid;

5-methyl-3-(2-methyl-propyl)-1-(4-carbamimidoyl-phenyl)-2-(2-carbamoyl-ethyl)-4,6-dioxo-octahydro-pyrrolo[3,4-c]pyrrole-1-carboxylic acid;

3-hydroxymethyl-5-methyl-1-(4-carbamimidoyl-phenyl)-2-(2-carbamoyl-ethyl)-4,6-dioxo-octahydro-pyrrolo[3,4-c]pyrrole-1-carboxylic acid;

3-benzyl-5-methyl-1-(4-carbamimidoyl-phenyl)-2-(2-carbamoyl-ethyl)-4,6-dioxo-octahydro-pyrrolo[3,4-c]pyrrole-1-carboxylic acid;

5-butyl-1-(4-carbamimidoyl-phenyl)-2-(2-carbamoyl-ethyl)-4,6-dioxo-octahydro-pyrrolo[3,4-c]pyrrole-1-carboxylic acid;

5-butyl-3-methyl-1-(4-carbamimidoyl-phenyl)-2-(2-carbamoyl-ethyl)-4,6-dioxo-octahydro-pyrrolo[3,4-c]pyrrole-1-carboxylic acid;

5-butyl-3-(prop-2-yl)-1-(4-carbamimidoyl-phenyl)-2-(2-carbamoyl-ethyl)-4,6-dioxo-octahydro-pyrrolo[3,4-c]pyrrole-1-carboxylic acid;

5-butyl-3-(2-methyl-propyl)-1-(4-carbamimidoyl-phenyl)-2-(2-carbamoyl-ethyl)-4,6-dioxo-octahydro-pyrrolo[3,4-c]pyrrole-1-carboxylic acid;

5-butyl-3-hydroxymethyl-1-(4-carbamimidoyl-phenyl)-2-(2-carbamoyl-ethyl)-4,6-dioxo-octahydro-pyrrolo[3,4-c]pyrrole-1-carboxylic acid;

3-benzyl-5-butyl-1-(4-carbamimidoyl-phenyl)-2-(2-carbamoyl-ethyl)-4,6-dioxo-octahydro-pyrrolo[3,4-c]pyrrole-1-carboxylic acid;

3-methyl-5-phenyl-1-(4-carbamimidoyl-phenyl)-2-(2-carbamoyl-ethyl)-4,6-dioxo-octahydro-pyrrolo[3,4-c]pyrrole-1-carboxylic acid;

5-phenyl-3-(prop-2-yl)-1-(4-carbamimidoyl-phenyl)-2-(2-carbamoyl-ethyl)-4,6-dioxo-octahydro-pyrrolo[3,4-c]pyrrole-1-carboxylic acid;

3-(2-methyl-propyl)-5-phenyl-1-(4-carbamimidoyl-phenyl)-2-(2-carbamoyl-ethyl)-4,6-dioxo-octahydro-pyrrolo[3,4-c]pyrrole-1-carboxylic acid;

3-hydroxymethyl-5-phenyl-1-(4-carbamimidoyl-phenyl)-2-(2-carbamoyl-ethyl)-4,6-dioxo-octahydro-pyrrolo[3,4-c]pyrrole-1-carboxylic acid;

3-benzyl-5-phenyl-1-(4-carbamimidoyl-phenyl)-2-(2-carbamoyl-ethyl)-4,6-dioxo-octahydro-pyrrolo[3,4-c]pyrrole-1-carboxylic acid;

5-benzyl-3-methyl-1-(4-carbamimidoyl-phenyl)-2-(2-carbamoyl-ethyl)-4,6-dioxo-octahydro-pyrrolo[3,4-c]pyrrole-1-carboxylic acid;

5-benzyl-3-(2-methyl-propyl)-1-(4-carbamimidoyl-phenyl)-2-(2-carbamoyl-ethyl)-4,6-dioxo-octahydro-pyrrolo[3,4-c]pyrrole-1-carboxylic acid;

5-benzyl-3-hydroxymethyl-1-(4-carbamimidoyl-phenyl)-2-(2-carbamoyl-ethyl)-4,6-dioxo-octahydro-pyrrolo[3,4-c]pyrrole-1-carboxylic acid;

3,5-dibenzyl-1-(4-carbamimidoyl-phenyl)-2-(2-carbamoyl-ethyl)-4,6-dioxo-octahydro-pyrrolo[3,4-c]pyrrole-1-carboxylic acid;

5-(2-phenyl-ethyl)-1-(4-carbamimidoyl-phenyl)-2-(2-carbamoyl-ethyl)-4,6-dioxo-octahydro-pyrrolo[3,4-c]pyrrole-1-carboxylic acid;

5-(2-phenyl-ethyl)-3-(prop-2-yl)-1-(4-carbamimidoyl-phenyl)- 2-(2-carbamoyl-ethyl)-4,6-dioxo-octahydro-pyrrolo[3,4-c]pyrrole-1-carboxylic acid;

3-(2-methyl-propyl)-5-(2-phenyl-ethyl)-1-(4-carbamimidoyl-phenyl)-2-(2-carbamoyl-ethyl)-4,6-dioxo-octahydro-pyrrolo[3,4-c]-pyrrole-1-carboxylic acid;

3-hydroxymethyl-5-(2-phenyl-ethyl)-1-(4-carbamimidoyl-phenyl)-2-(2-carbamoyl-ethyl)-4,6-dioxo-octahydro-pyrrolo[3,4-c]-pyrrole-1-carboxylic acid;

3-benzyl-1-(4-carbamimidoyl-phenyl)-2-(2-carbamoyl-ethyl)-4,6-dioxo-octahydro-5-(2-phenyl-ethyl)-pyrrolo[3,4-c]pyrrole-3-carboxylic acid; and, respectively, (3aRS,4SR,8aRS,8bSR)-4-(2-butyl-1,3-dioxo-decahydro-pyrrolo[3,4-a]pyrrolizin-4-yl)-benzimidamide;

(3aRS,4RS,9aSR,9bSR)-4-(2-benzyl-1,3-dioxo-decahydro-pyrrolo[3,4-c]indolizin-4-yl)-benzimidamide;

(3aRS,4SR,9aRS,9bSR)-4-(2-benzyl-1,3-dioxo-decahydro-pyrrolo[3,4-c]indolizin-4-yl)-benzimidamide;

(3aRS,4RS,8aSR,8bSR)-4-[2-(benzo[1,3]dioxol-5-ylmethyl)-1,3-dioxo-decahydro-pyrrolo[3,4-a]pyrrolizin-4-yl]-benzimidamide;

(5RS,5aRS,8aSR,8bRS)-4-[7-(benzo[1,3]dioxol-5-ylmethyl)-6,8-dioxo-octahydro-pyrrolo[3',4':3,4]pyrrolo[1,2-c]thiazol-5-yl]-benzimidamide;

(3aS,4R,8S,8aS,8bR)-4-[2-(benzo[1,3]dioxol-5-ylmethyl)-8-methyl-1,3-dioxo-decahydro-pyrrolo[3,4-a]pyrrolizin-4-yl]-benzimidamide;

(3aR,4R,7R,8aS,8bS)-4-(2-benzyl-7-hydroxy-1,3-dioxo-decahydro-pyrrolo[3,4-a]pyrrolizin-4-yl)-benzimidamide;

methyl (R)-2-[(3aS,4S,8aR,8bR)- and -(3aR,4R,8aS,8bS)-4-(4-carbamimidoyl-phenyl)-1,3-dioxo-decahydro-pyrrolo[3,4-a]-pyrrolizin-2-yl]-3-phenyl-propionate;

methyl (R)-2-[(3aR,4S,8aR,8bS)- and -(3aS,4R,8aR,8bR)-4-(4-carbamimidoyl-phenyl)-1,3-dioxo-decahydro-pyrrolo[3,4-a]-pyrrolizin-2-yl]-3-phenyl-propionate;

(1S,2S,5R,5aS,8aR)-[7-benzyl-5-(4-carbamimidoyl-phenyl)-2-(propen- 2-yl)-6,8-dioxo-decahydro-pyrrolo[3,4-a]pyrrolizin-1-yl]-acetic acid;

(5RS,5aSR,8aRS,8bRS)-4-[7-(benzo[1,3]dioxol-5-ylmethyl)-2,2,6,8-tetraoxo-octahydro-pyrrolo[3',4':3,4]pyrrolo[1,2-c]thiazol-5-yl]-benzimidamide;

(3aRS,4SR,8aRS,8bSR)-N-[4-(2-benzyl-1,3-dioxo-decahydro-pyrrolo[3,4-a]pyrrolizin-1-yl)-phenyl]-guanidine;

(3aRS,4SR,8aRS,8bSR)-N-[4-[2-(benzo[1,3]dioxol-5-ylmethyl)-1,3-dioxo-decahydro-pyrrolo[3,4-a]pyrrolizin-4-yl]-phenyl]-guanidine;

(3aRS,4SR,8aRS,8bSR)-2-benzyl-4-(2,4-diamino-quinazolin-6-yl)-hexahydro-pyrrolo[3,4-a]pyrrolizine-1,3-dione;

(3aRS,4RS,8aSR,8bSR)-2-benzyl-4-(2,4-diamino-quinazolin-6-yl)-hexahydro-pyrrolo[3,4-a]pyrrolizine-1,3-dione;

(3aRS,4SR,8aRS,8bSR)-2-benzyl-4-(2,4-diamino-quinazolin-7-yl)-hexahydro-pyrrolo[3,4-a]pyrrolizine-1,3-dione;

[2-methyl-4-(4-carbamimidoyl-phenyl)-1,3-dioxo-decahydro-pyrrolo[3,4-a]pyrrolizin-8a-yl]-carboxylic acid;

[2-butyl-4-(4-carbamimidoyl-phenyl)-1,3-dioxo-decahydro-pyrrolo[3,4-a]pyrrolizin-8a-yl]-carboxylic acid;

[2-cyclohexylmethyl-4-(4-carbamimidoyl-phenyl)-1,3-dioxo-decahydro-pyrrolo[3,4-a]pyrrolizin-8a-yl]-carboxylic acid;

[2-phenyl-4-(4-carbamimidoyl-phenyl)-1,3-dioxo-decahydro-pyrrolo[3,4-a]pyrrolizin-8a-yl]-carboxylic acid;

[2-benzyl-4-(4-carbamimidoyl-phenyl)-1,3-dioxo-decahydro-pyrrolo[3,4-a]pyrrolizin-8a-yl]-carboxylic acid; and 2-[4-(4-carbamimidoyl-phenyl)-1,3-dioxo-decahydro-pyrrolo[3,4-a]pyrrolizin-2-yl]-3-phenyl-propionamide.

Further examples of compounds of Formula I are:

(1RS,3RS,3aSR,6aRS)-4-[3-(Benzyloxy-methyl)-5-(4-nitro-benzyl)-4,6-dioxo-octahydro-pyrrolo[3,4-c]pyrrol-1-yl]-benzimidamide and (1RS,3RS,3aSR,6aRS)-4-[5-(4-amino-benzyl)-3-(benzyloxy-methyl)-4,6-dioxo-octahydro-pyrrolo[3,4-c]pyrrol-1-yl]-benzimidamide.

The compounds in accordance with the invention can be manufactured by a) reacting a maleimide of the formula

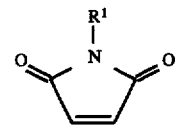

II with an α-aminocarboxylic acid of the formula

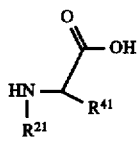

or a functional derivative thereof,
and a compound of Formula IV

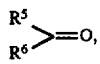

wherein $R^{21}$ is H, lower-alkyl, aryl, heteroaryl, cycloalkyl or lower-alkyl which is substituted with $R^{10}$ and optionally $R^{11}$ or with $R^{11}$ and optionally $R^{10}$; and $R^{41}$ is H, lower-alkyl, aryl, aralkyl, cycloalkyl, heteroaryl or lower-alkyl substituted with OH, $SO_2H$, $SO_3H$, guanidino, aryl-lower-alkoxy or lower-alkyl-(O or S); or $R^{21}$ and $R^{41}$ together form a group $G^1$, and $G^1$ is a tri- or tetramethylene group wherein one methylene group is optionally replaced by S, or is optionally substituted with OH, lower-alkyl, lower-alkenyl or carboxy-lower-alkyl, or wherein one methylene group is optionally substituted with lower-alkenyl and another methylene group is optionally substituted with carboxy-lower-alkyl;

with the proviso that at least one of $R^1$, $R^{21}$, $R^{41}$, $R^5$ and $R^6$ is a group substituted with amino, amidino, guanidino or N-hydroxyamidino, b) for the manufacture of a compound of Formula I in which one of $R^5$ and $R^6$ is a phenyl or lower-alkyl group substituted by amidino, N-hydroxyamidino or guanidino, amidinating; N-hydroxyamidinating or guanidinating a compound corresponding to the compound of Formula I which contains a phenyl or lower-alkyl group substituted by CN or $NO_2$ in place of the phenyl or lower-alkyl group substituted by amidino, N-hydroxyamidino or guanidino; and c) if desired, functionally modifying a reactive group present in a compound of Formula I; and d) if desired, converting a compound of Formula I into a physiologically compatible salt or converting a salt of a compound of Formula I into the free acid or base.

Functional derivatives of an acid of Formula III include lower-alkyl esters as well as acids of Formula III bonded as an ester or amide to a solid carrier, for example, a resin. The reaction a) of the maleimide of Formula II with the α-amino acid of Formula III and the ketone or the aldehyde of Formula IV is conveniently carried out in a solvent such as DMF, DMSO, acetonitrile, THF, diethyl ether, benzene, toluene, acetic acid, methanol or ethanol at a temperature between 0° C. and 160° C. Preferably the reaction is carried out either at elevated temperature in DMF, DMSO or toluene. Most preferably, the reaction can be carried out at an elevated temperature in methanol with the addition of catalytic amounts of acetic acid or also in acetonitrile at room temperature with the addition of silver acetate and a tertiary nitrogen base such as triethylamine, diazabicyclooctane or ethylmorpholine. Reaction a) can be carried out especially advantageously by bonding either the maleimide of Formula II or the α-aminocarboxylic acid of Formula III via a carboxy group present in the residue $R^2$, or via the carboxy group of the α-amino carboxylic acid of Formula III to a solid phase such as a polystyrene resin with the formation of an ester or amide group and by using in the reaction the ketone or the aldehyde of Formula IV and the α-amino carboxylic acid of Formula III or the maleimide of Formula II which is not bonded to the solid phase in an up to 20-fold excess in comparison to the compound bonded to the solid phase.

In order to convert a cyano group into the amidino group according to process variant b), the starting nitrile in a solvent such as ethanol or methanol or a solvent mixture such as chloroform and methanol or chloroform and ethanol can be gassed with a dry hydrogen chloride stream, conveniently at a temperature below 10° C. The reaction solution is treated with a solvent such as diethyl ether and the thus-precipitated intermediate, an imidoether hydrochloride, is filtered off. Thereafter, the intermediate can be dissolved in water, neutralized with a base such as sodium carbonate or sodium hydroxide and extracted from the aqueous phase with a solvent such as dichloromethane, chloroform or ethyl acetate. The thus-obtained imidoether is treated in a solvent such as methanol or ethanol either with gaseous ammonia or an ammonium salt such as ammonium chloride, conveniently at a temperature up to 80° C. Alternatively, the filtered-off intermediate can be treated similarly with gaseous ammonia or an ammonium salt in methanol or ethanol. In order to convert a cyano group into a N-hydroxyamidino group, the starting nitrile is dissolved in a solvent such as DMF and added to a reaction solution of an inorganic base such as sodium hydride or sodium hydroxide, and hydroxylamine or a salt thereof with an inorganic acid such as hydroxylamine hydrochloride, conveniently at a temperature below 0° C. In order to convert the nitro group into a guanidino group, the starting material is dissolved in a solvent such as ethanol or acetic acid and hydrogenated under a hydrogen atmosphere in the presence of a catalyst such as Pd/C. The thus-obtained amine is reacted in a solvent such as DMF or methanol in the presence of a base such as triethylamine with formamidinesulfonic acid or 3,5-dimethyl-1-pyrazolylformamidinium nitrate, conveniently at a temperature up to 80° C.

The following are examples of functional modifications c) of reactive groups present in a compound of Formula I:

A compound of Formula I in which $R^2$ is H can be reacted with an agent yielding the group $R^2$, wherein $R^2$ is not H. Thus, such a compound in formic acid can be methylated with a formalin solution at elevated temperature or lower alkenoylated with a lower-alkanoyl chloride in a solvent such as pyridine or dichloromethane in the presence of an organic base such as pyridine, triethylamine, diazabicyclooctane or ethylmorpholine.

A compound of Formula I in which a group G present contains a sulfur atom can be converted with a oxidizing agent such as a peracid, for example 3-chloroperbenzoic acid, in a solvent such as methanol, ethanol, dichloromethane or dioxan firstly into the corresponding sulfoxide and then, if desired, into the sulfone.

The compounds of Formulae of II, III and IV as well as the starting materials containing a CN or $NO_2$ group used in process variant b) are known or can be prepared in analogy to the known compounds. Thus, the starting nitrile can be prepared by reacting a corresponding bromide in a solvent such as DMF with copper cyanide or an alkali cyanide and a copper salt at a temperature between 100° and 160° C.

Moreover, many of the Examples hereinafter contain detailed information concerning the preparation of certain starting materials and intermediates.

The compounds of Formula I, their solvates and their salts inhibit not only thrombin-induced and factor Xa-induced platelet aggregation, but also thrombin-induced clotting of fibrinogen in blood plasma. The said compounds influence not only platelet-induced, but also plasmatic blood clotting. They therefore prevent especially the formation of hyaline thrombi and of platelet-rich thrombi and can be used in the control or prevention of illnesses such as thrombosis, stroke, cardiac infarct, inflammation and arteriosclerosis. Further, these compounds have an effect on tumour cells and prevent the formation of metastases. Accordingly, they can also be used as antitumour agents.

The detection of the inhibition of the amidolytic activity of thrombin by the above compounds was demonstrated as described hereinafter.

The measurements were carried out on microtitre plates at room temperature. For this, in each well of the plate 150 ml of buffer (50 mM Tris, 100 mM NaCl, 0.1% polyethylene glycol; pH 7.8) were mixed with 50 ml of the inhibitor dissolved in DMSO and diluted in the buffer and 25 ml of human thrombin (0.5 nM final conc.). After incubation for 10 minutes the reaction was started by the addition of the chromogenic substrate H-D-Phe-Pip-Arg-paranitroaniline (10 or 50 µM final concentration), in which Pip represents the characterizing group 2-piperidylenecarbonyl of the α-aminoacid H-Pip-OH, which is (S)-piperidine-2-carboxylic acid (or L-homoproline). The hydrolysis of the substrate was followed spectrophotometrically on a kinetic microtitre plate reader for 5 minutes. After graphic presentation of the inhibition curves the $K_i$ values were determined according to the method described in Biochem J. 55, 1955, 170–171. The results are presented in Table I below.

TABLE I

| Product of Example | $K_i$ (µM) |
| --- | --- |
| 4.A)a) | 0.67 |
| 4.A)f) | 0.22 |
| 4.A)g) | 0.09 |
| 7.A)g) | 0.35 |
| 7.A)i) | 0.44 |
| 7.A)o) | 0.67 |
| 9 | 0.11 |

The detection of the inhibition of the amidolytic activity of Factor Xa was demonstrated in a manner analogous to that of thrombin, but using the chromogenic substrate Bz-Ile-Glu-Gly-Arg-paranitroaniline (167 µM final concentration). The results are presented in Table II below.

TABLE II

| Product of Example | $K_i$ (µM) |
| --- | --- |
| 19 | 0.076 |
| 18 | 0.098 |

Further objects of the present invention are medicaments comprising compounds of Formula I and solvates or salts thereof. Also an object of the present invention is a process for the production of such medicaments, which comprises bringing one or more other therapeutically valuable substances into a galenical administration form. These medicaments can be administered orally, for example, in the form of dragées, hard and soft gelatine capsules, solutions, emulsions or suspensions; rectally, for example, in the form of suppositories; as a spray; or parenterally, for example, in the form of injection solutions.

The active ingredient can be mixed with pharmaceutically inert, inorganic or organic excipients for the production of tablets, coated tablets, dragées and hard gelatine capsules. Lactose, corn starch or derivatives thereof, talc, stearic acid or its salts can be used e.g. as such excipients for tablets, coated tablets, dragées and hard gelatine capsules. Suitable excipients for soft gelatine capsules are e.g. vegetable oils, waxes, fats, semi-solid and liquid polyols; depending on the nature of the active ingredient no excipients are, however, usually required in the case of soft gelatine capsules. Suitable excipients for the production of solutions and syrups are e.g. water, polyols, sucrose, invert sugar and glucose, suitable excipients for injection solutions are e.g. water, alcohols, polyols, glycerol and vegetable oils and suitable excipients for suppositories are natural and hardened oils, waxes, fats, semi-liquid or liquid polyols. The pharmaceutical preparations can also contain preservatives, solubilizers, stabilizers, wetting agents, emulsifiers, sweeteners, colorants, flavorants, salts for varying the osmotic pressure, buffers, masking agents or antioxidants.

For the control or prevention of the illnesses mentioned above, the dosage of the active ingredient can vary within wide limits and will, of course, be fitted to the individual requirements in each particular case. In general, in the case of oral or parenteral administration a dosage of about 0.1 to 20 mg/kg, preferably of about 0.5 to 4 mg/kg, per day should be appropriate for adults, although the upper limit just given can also be exceeded or reduced when this is shown to be indicated.

EXAMPLE 1

871 mg (5 mmol) of arginine, 530 mg (5 mmol) of benzaldehyde, 1.122 g (6 mmol) of N-benzylmaleimide and 25 drops of acetic acid were heated under reflux in 25 ml of methanol for 60 hours. After cooling the colourless precipitate was filtered off under suction and washed with ether. 1.367 g of (1RS,3SR,3aRS,6aSR)-5-benzyl-1-(3-guanidinopropyl)-4,6-dioxo-octahydro-3-phenyl-pyrrolo[3,4-c]-pyrrole-1-carboxylic acid acetate (54%) were isolated as a colourless powder. M.p.: from 195° C. decomposition. ISP-MS: 450.4 ([M+H]$^+$, 100).

EXAMPLE 2

806 mg of (1RS,3aSR,6aRS)-4-(5-benzyl-2,3,3-trimethyl-4,6-dioxo-octahydro-pyrrolo[3,4-c]pyrrol-1-ylmethyl)-benzonitrile were dissolved in 5 ml of dry chloroform and 1 ml of methanol. Dry HCl was introduced at 0° C. for 10 minutes. Thereafter, the reaction mixture was left to stand at 4° C. for 2 days. The hydrochloride of the imidoether was precipitated by the addition of diethyl ether. This solid was dried and treated with 8 ml of 5% NaHCO$_3$ solution and 20 ml of chloroform. The mixture was shaken rapidly and the aqueous phase was extracted twice with chloroform. The organic phase was dried with Na$_2$SO$_4$ and the solvent was removed. The residue was dissolved in 7 ml of methanol, 150 mg of NH$_4$Cl in 1.5 ml of H$_2$O were added and the mixture was stirred at 65° C. for 3.5 hours. After cooling the ammonium chloride was precipitated with acetone and filtered off. The solvent was removed, the residue was dissolved in ethanol and the amidine was precipitated slowly with diethyl ether. 483 mg of (1RS,3aSR,6aRS)-4-(5-benzyl-2,3,3-trimethyl-4,6-dioxo-octahydro-pyrrolo[3,4-c]pyrrol-1-ylmethyl)-benzimidamide acetate were isolated as a yellowish powder. M.p.: 205°–207° C. ISP-MS: 405.4 ([M+H]$^+$, 100).

Preparation of the starting material:

2.a) 8.83 g (36.2 mmol) of 4-bromophenylalanine, 4.74 g (81.7 mmol) acetone and 7.00 g (37.43 mmol) of N-benzylmaleimide were heated under reflux for 68 hours. in 140 ml of toluene with the addition of molecular sieve A4. The solvent was removed in a vacuum and the residue was separated chromatographically (hexane/ethyl acetate 1:1+1% triethylamine). As the main product there were obtained 3.88 g of (3aRS, 4RS,6aSR)-2-benzyl-4-(4-bromo-benzyl)-6,6-dimethyl-tetrahydro-pyrrolo[3,4-c]pyrrol-1,3-dione as a colourless oil which, after the addition of a small amount of methanol, crystallized overnight to colourless needles. M.p.: 142°–143° C. FAB-MS: 427 ([M+H]+, 58); 257 (66); 240 (8); 200 (6); 91 (58). 2.12 g of (3aRS,4SR,6aSR)-2-benzyl-4-(4-bromobenzyl)-6,6-dimethyl-tetrahydro-pyrrolo[3,4-c]pyrrole-1,3-dione were obtained as a byproduct as a colourless oil. FAB-MS: 427 ([M+H]+, 88); 257 (89); 91 (100).

2.b) A mixture of 3.88 g (9.1 mmol) of (3aRS,4RS,6aSR)-2-benzyl-4-(4-bromo-benzyl)-6,6-dimethyl-tetrahydro-pyrrolo[3,4-c]pyrrole-1,3-dione, 85% formic acid (4.9 g, 90 mmol) and 35% formalin solution (2.6 g, 30 mmol) were heated to 100° C. for 5.5 hours. After cooling 1N NaOH (50 ml) was added and the mixture was extracted four times with dichloromethane. The organic phase was concentrated and the residue was separated chromatographically (hexane/ethyl acetate 3:1+1% triethylamine). 3.45 g of (3aRS, 4RS,6aSR)-2-benzyl-4-(4-bromobenzyl)-5,6,6-trimethyl-tetrahydro-pyrrolo[3,4-c]pyrrole-1,3-dione were isolated as a yellowish oil. FAB-MS: 441 ([M+H]+, 40); 271 (100); 212 (5); 169 (11); 136 (14); 110 (26); 91 (42).

2.c) 3.45 g (7.82 mmol) of (3aRS,4RS,6aSR)-2-benzyl-4-(4-bromobenzyl)-5,6,6-trimethyl-tetrahydro-pyrrolo[3,4-c]pyrrole-1,3-dione and 3.52 g (39.1 mmol) of copper(I) cyanide were suspended in 150 ml of DMF under argon and heated under reflux for 56 hours. After cooling about 100 ml of DMF were removed, then 150 ml of dichloromethane and 60 ml of concentrated aqueous ammonia solution were added. The mixture was stirred vigorously for a few hours. The blue aqueous phase was separated and the organic phase was washed twice with ammonia solution and once with water. The solvent was removed and the residue was purified chromatographically (hexane/ethyl acetate 1:1+1% triethylamine). 1.91 g of (1RS,3aSR,6aRS)-4-(5-benzyl-2,3,3-trimethyl-4,6-dioxo-octahydro-pyrrolo[3,4-c]pyrrol-1-ylmethyl)-benzonitrile were isolated as a yellowish oil. FAB-MS: 775 ([2M+H]+, 1); 663 (2); 388 ([M+H]+, 58); 271 (100); 91 (42).

EXAMPLE 3

2.19 g (31.56 mmol) of hydroxylamine hydrochloride were suspended in 8 ml of DMF and cooled to 0° C. 0.79 g (26.3 mmol) of 80% sodium hydride was added slowly. 1.02 g (2.63 mmol) of (1RS, 3aSR,6aRS)-4-(5-benzyl-2,3,3-trimethyl-4,6-dioxo-octahydro-pyrrolo[3,4-c]pyrrol-1-ylmethyl)-benzonitrile were dissolved in DMF and added to the reaction mixture. The cooling was then no longer applied. The mixture was stirred at room temperature for 2 days. Thereafter, it was filtered and the DMF was removed in a high vacuum. The mixture was purified chromatographically (RP18, gradient from water to methanol). 1.08 g (97%) of (3aRS,4RS,6aSR)-4-[4-(amino-hydroxyimino-methyl)-benzyl]-2-benzyl-5,6,6-trimethyl-tetrahydro-pyrrolo[3,4-c]pyrrole-1,3-dione were isolated as a colourless powder. M.p.: 189°–192° C. ISP-MS: 421.5 ([M+H]+, 100).

EXAMPLE 4

The following compounds were prepared analogously to Example 2:

4.A)a) (1RS,3SR,3aRS,6aSR)-4-(5-Benzyl-2,3-dimethyl-4,6-dioxo-octahydro-pyrrolo[3,4-c]pyrrol-1-yl)-benzimidamide hydrochloride. M.p.: 201°–203° C. ISP-MS: 377.4 ([M+H]+, 100).

4.A)b) (1RS,3SR,3aRS,6aSR)-4-(5-Benzyl-3-methyl-4,6-dioxo-octahydro-pyrrolo[3,4-c]pyrrol-1-yl)-benzimidamide hydrochloride. M.p.: 188°–191° C. ISP-MS: 363.4 ([M+H]+, 100).

4.A)c) (1RS,3SR,3aRS,6aSR)-4-(2-Acetyl-5-benzyl-3-methyl-4,6-dioxo-octahydro -pyrrolo[3,4-c]pyrrol-1-yl)-benzimidamide hydrochloride. M.p.: 204°–208° C. (acetone). ISP-MS: 405 ([M+H]+, 100).

4.A)d) (1RS,3SR,3aRS,6aSR)-4-(5-Butyl-2,3-dimethyl-4,6-dioxo-octahydro-pyrrolo[3,4-c]pyrrol-1-yl)-benzimidamide hydrochloride. M.p.: 171°–176° C. ISP-MS: 343.4 ([M+H]+, 100).

4.A)e) (1RS,3SR,3aRS,6aSR)-4-(2-Acetyl-5-butyl-3-methyl-4,6-dioxo-octahydro -pyrrolo[3,4-c]pyrrol-1-yl)-benzimidamide hydrochloride. M.p.: 203°–206° C. ISP-MS: 371.4 ([M+H]+, 100).

4.A)f) (3aRS,4SR,8aRS,8bSR)-4-(2-Benzyl-1,3-dioxo-decahydro-pyrrolo[3,4-a]pyrrolizin-4-yl)-benzimidamide hydrochloride. M.p.: 202°–205° C. ISP-MS: 389.4 ([M+H]+, 100); 309.4 (20); 195.4 (58); 158.2 (40).

4.A)g) (3aRS,4SR,8aRS,8bSR)-4-[2-(Benzo[1,3]dioxol-5-ylmethyl)-1,3-dioxo-decahydro-pyrrolo[3,4-a]pyrrolizin-4-yl]-benzimidamide hydrochloride. M.p.: 177°–181° C. ISP-MS: 433.4 ([M+H]+, 100).

Preparation of the starting materials:

4.B)a)1) (3aRS,4SR,6RS,6aSR)-2-Benzyl-4-(4-bromo-phenyl)-6-methyl-tetrahydro -pyrrolo[3,4-c]pyrrole-1,3-dione was prepared from N-benzylmaleimide, D,L-alanine and 4-bromobenzaldehyde in an analogous manner to Example 2.a). 47% were isolated as colourless crystals. M.p.: 170°–172° C. FAB-MS: 799 ([2M+3H]+, 10); 552 (3); (399 ([M+H]+, 100); 238 (9); 211 (29); 91 (61).

4.B)a)2) (3aRS,4SR,6RS,6aSR)-2-Benzyl-4-(4-bromo-phenyl)-5,6-dimethyl -tetrahydro-pyrrolo[3,4-c]pyrrole-1,3-dione was prepared from (3aRS,4SR,6RS,6aSR)-2-benzyl-4-(4-bromo-phenyl)-6-methyl-tetrahydro-pyrrolo[3,4-c]pyrrole-1,3-dione in an analogous manner to Example 2.b). 96% were isolated as colourless crystals. M.p.: 166°–168° C. FAB-MS: 827 ([2M+3H]+, 3); 566 (2); 413 (M+H]+, 100); 397 (31); 250 (8); 225 (12); 91 (46).

4.B)a)3) 400 mg (0.96 mmol) of (3aRS,4SR,6RS,6aSR)-2-benzyl-4-(4-bromo-phenyl)-5,6-dimethyl-tetrahydro-pyrrolo[3,4-c]pyrrole-1,3-dione and 360 mg (4.02 mmol) of copper(I) cyanide were suspended in 25 ml of DMF and heated under reflux and under argon for 18 hours. After cooling about 15 ml of DMF were removed, then 30 ml of dichloromethane and 20 ml of concentrated aqueous ammonia solution were added. The mixture was stirred vigorously for a few hours. The blue aqueous phase was separated and the organic phase was washed twice with ammonia solution and once with water. The solvent was removed and the residue was purified chromatographically (hexane/ethyl acetate 2:1+1% triethylamine). 293 mg of (1RS, 3SR,3aRS,6aSR)-4-(5-benzyl-2,3-dimethyl-4,6-dioxo-octahydro-pyrrolo[3,4-c]pyrrol-1-yl)-benzonitrile (85%) were isolated as colourless crystals. M.p.: 188°–190° C. (ethyl acetate). FAB-MS: 719 ([2M+H]+, 3); 512 (3); 360 ([M+H]+, 100); 344 (41); 289 (15); 107 (37); 91 (56).

4.B)b) (1RS,3SR,3aRS,6aSR)-4-(5-Benzyl-3-methyl-4,6-dioxo-octahydro-pyrrolo[3,4-c]pyrrol-1-yl)-benzonitrile was prepared from 4-cyano-benzaldehyde, D,L-alanine and N-benzylmaleimide in an analogous manner to Example 2.a). M.p.: 169°–170° C. ISP-MS: 346.3 ([M+H]$^+$, 45); 279.3 (26); 267.2 (18); 199.3 (13); 171.4 (23); 158.2 (28); 149.2 (25); 134.1 (17).

4.B)c) A solution of 3.46 g (10 mmol) of (1RS,3SR,3aRS,6aSR)-4-(5-benzyl-3-methyl-4,6-dioxo-octahydro-pyrrolo[3,4-c]pyrrol-1-yl)-benzonitrile in acetonitrile (10 ml) was treated with pyridine (20 mmol). Acetic anhydride (20 mmol) was slowly added dropwise while cooling with ice. The cooling was removed and the reaction mixture was stirred for a further 1.5 hours. Thereafter, the reaction mixture was poured into saturated NaCl solution and extracted with dichloromethane. The solvent was removed and the residue was separated chromatographically (hexane:ethyl acetate=1:1). (1RS,3SR,3aRS,6aSR)-4-(2-Acetyl-5-benzyl-3-methyl-4,6-dioxo-octahydro-pyrrolo[3,4-c]pyrrol-1-yl)-benzonitrile (83%) was isolated as a colourless solid. M.p.: 107°–109° C. EI-MS: 387 ([M]$^+$, 72); 344 (35); 320 (28); 254 (18); 183 (16); 169 (17); 158 (53); 91 (86); 43 (100).

4.B)d)1) (1RS,3SR,3aRS,6aSR)-4-(5-Butyl-3-methyl-4,6-dioxo-octahydro-pyrrolo[3,4-c]pyrrol-1-yl)-benzonitrile was prepared in an analogous manner to Example 2.b) from N-butylmaleimide, D,L-alanine and 4-cyano-benzaldehyde. A yellowish oil was isolated in 65% yield. EI-MS: 311 (M$^+$, 12); 296 (9); 183 (8); 169 (13); 158 (100); 143 (5); 115 (4); 82 (5).

4.B)d)2) A mixture of 2.84 g of (1RS,3SR,3aRS,6aSR)-4-(5-butyl-3-methyl-4,6-dioxo-octahydro-pyrrolo[3,4-c]pyrrol-1-yl)-benzonitrile, 85% formic acid (4.9 g, 90 mmol) and 35% formalin solution (2.6 g, 30 mmol) were heated to 100° C. for 5.5 hours. After cooling 1N NaOH (50 ml) was added and the mixture was extracted four times with dichloromethane. The organic phase was concentrated and the residue was separated chromatographically (hexane/ethyl acetate 3:1+1% triethylamine). 2.52 g of (1RS,3SR,3aRS,6aSR)-4-(5-butyl-2,3-dimethyl-4,6-dioxo-octahydro-pyrrolo[3,4-c]pyrrol-1-yl)-benzonitrile (85%) were isolated as a colourless oil. EI-MS: 325 (M$^+$, 8); 310 (95); 223 (10); 183 (24); 171 (40); 157 (10); 143 (9); 70 (15); 56 (17); 43 (100).

4.B)e) (1RS,3SR,3aRS,6aSR)-4-(2-Acetyl-5-butyl-3-methyl-4,6-dioxo-octahydro -pyrrolo[3,4-c]pyrrol-1-yl)-benzonitrile was prepared in an analogous manner to Example 4.B)c). 2.71 g (77%) were isolated as a colourless solid. M.p.: 140°–141° C. (ethyl acetate). ISP-MS: 354.3 ([M+H]$^+$, 100); 158.1 (30).

4.B)f) A mixture of L-proline (20 mmol), 4-cyano-benzaldehyde (20 mmol) and N-benzylmaleimide (20 mmol) in DMF (20 ml) was heated to 80° C. for 5 hours. The solvent was removed in a high vacuum and the residue was separated chromatographically over silica gel (eluent hexane:ethyl acetate=1:1+1% triethylamine). (3aRS,4SR,8aRS,8bSR)-4-(2-Benzyl-1,3-dioxo-decahydro-pyrrolo[3,4-a]pyrrolizin-4-yl)benzonitrile was isolated in 32% yield as colourless crystals. M.p.: 191°–193° C. (methanol). EI-MS: 371 ([M]$^+$, 7); 184 (100); 156 (11); 91 (12)

4.B)g) A diastereomeric mixture of 4-(decahydro-2-piperonyl-1,3-dioxo-pyrrolo[3,4-a]pyrrolizin-4-yl)-benzonitrile was prepared in an analogous manner to Example 4.B)f) from L-proline, N-piperonyl-maleimide and 4-cyano-benzaldehyde and was separated by chromatography on silica gel (eluent hexane-:ethyl acetate=1:1+1% triethylamine). (3aRS,4SR,8aRS,8bSR)-4-[2-(Benzo[1,3]dioxol-5-ylmethyl)-1,3-dioxo-decahydro-pyrrolo[3,4-a]pyrrolizin-4-yl]-benzonitrile was isolated in 37% yield as colourless needles. M.p.: 176°–179° C. (methanol). ISP-MS: 416.4 ([M+H]$^+$, 100); 289.4 (15); 277.3 (55); 267.3 (24).

50% of (3aRS,4RS,8aSR,8bSR)-4-[2-(benzo[1,3]dioxol-5-ylmethyl)-1,3-dioxo-decahydro-pyrrolo[3,4-a]pyrrolizin-4-yl]-benzonitrile were also isolated as a yellowish foam. M.p.: 61°–63° C. ISP-MS: 416.4 ([M+H]$^+$, 100).

EXAMPLE 5

841 mg (12.12 mmol) of hydroxylamine hydrochloride were suspended in 4 ml of DMF and cooled to 0° C. 303 mg (10.1 mmol) of 80% sodium hydride were added slowly. 365 mg (1.01 mmol) of (1RS,3SR,3aRS,6aSR)-4-(5-benzyl-2,3-dimethyl-4,6-dioxo-octahydro-pyrrolo[3,4-c]pyrrol-1-yl)-benzonitrile were dissolved in DMF and added to the reaction mixture. The cooling was thereafter no longer renewed. The mixture was stirred at room temperature for 5 days. Thereafter, it was filtered and the solvent was removed in a high vacuum. The mixture was purified chromatographically (RP18, gradient from water to methanol). 191 mg (48%) of (3aRS,4SR,6RS,6aSR)-4-[4-(amino-hydroxyimino-methyl)-phenyl]-2-benzyl-5,6-dimethyl-tetrahydro-pyrrolo[3,4-c]pyrrole-1,3-dione were isolated as a colourless powder. M.p.: 194°–196° C. ISP-MS: 393 ([M+H]$^+$, 100); 303 (20); 219 (10).

EXAMPLE 6

800 mg of (1RS,3SR,3aRS,6aSR)-4-(5-butyl-3-methyl-4,6-dioxo-octahydro-pyrrolo[3,4-c]pyrrol-1-yl)-benzonitrile were dissolved in 5 ml of dry chloroform and 1 ml of methanol. Dry HCl was introduced at 0° C. for 10 minutes. Thereafter, the reaction mixture was left to stand at 4° C. for 2 days. The hydrochloride of the imidoether was precipitated by the addition of diethyl ether. This solid was treated with a saturated ammonia solution in methanol and refluxed for 2 hours. Thereafter, the solvent was removed and the residue was chromatographed on RP-18 silica gel (gradient from water to methanol). (1RS,3SR,3aRS,6aSR)-4-(5-Butyl-3-methyl-4,6-dioxo-octahydro-pyrrolo[3,4-c]pyrrol-1-yl)-benzimidamide hydrochloride was isolated in 55% yield as a colourless solid. M.p.: from 180° C. dec. ISP-MS: 329.4 ([M+H]$^+$, 100).

EXAMPLE 7

The following compounds were prepared analogously to Example 6:

7.A)a) (1RS,3SR,3aRS,6aSR)-4-(5-Benzyl-3-isobutyl-4,6-dioxo-octahydro-pyrrolo[3,4-c]pyrrol-1-yl)-benzimidamide hydrochloride. Colourless foam. M.p.: 152°–157° C. ISP-MS: 405.4 ([M+H]$^+$, 100); 315.4 (26).

7.A)b) (1RS,3SR,3aRS,6aSR)-4-(5-Benzyl-3-isobutyl-2-methyl-4,6-dioxo-octahydro-pyrrolo[3,4-c]pyrrol-1-yl)-benzimidamide hydrochloride. Colourless foam. M.p.: 157°–162° C. ISP-MS: 419.5 ([M+H]$^+$, 100).

7.A)c) (3aRS,4SR,8aRS,8bSR)-4-(2-Butyl-1,3-dioxo-decahydro-pyrrolo[3,4-a]pyrrolizin-4-yl)-benzimidamide hydrochloride. Oil. ISP-MS: 355.4 ([M+H]$^+$, 100).

7.A)d) (3aRS,4RS,9aSR,9bSR)-4-(2-Benzyl-1,3-dioxo-decahydro-pyrrolo[3,4-c]indolizin-4-yl)-benzimidamide hydrochloride. Colourless foam. M.p.: >295° C. ISP-MS: 403.4 ([M+H]⁺, 100).

7.A)e) (3aRS,4SR,9aRS,9bSR)-4-(2-Benzyl-1,3-dioxo-decahydro-pyrrolo[3,4-c]indolizin-4-yl)-benzimidamide hydrochloride. Colourless foam. M.p.: 248°–250° C. ISP-MS: 403.4 ([M+H]⁺, 100).

7.A)f) (3aRS,4RS,8aSR,8bSR)-4-[2-(Benzo[1,3]dioxol-5-ylmethyl)-1,3-dioxo-decahydro-pyrrolo[3,4-a]pyrrolizin-4-yl]-benzimidamide hydrochloride. Colourless foam. M.p.: 195°–200° C. ISP-MS: 433.5 ([M+H]⁺, 100).

7.A)g) (3aRS,4SR,8aRS,8bSR)-4-(2-Cyclohexylmethyl-1,3-dioxo-decahydro-pyrrolo[3,4-a]pyrrolizin-4-yl)-benzimidamide hydrochloride. Yellowish solid. M.p.: 104°–110° C. ISP-MS: 395.4 ([M+H]⁺, 100).

7.A)h) (5RS,5aRS,8aSR,8bRS)-4-[7-(Benzo[1,3]dioxol-5-ylmethyl)-6,8-dioxo-octahydro-pyrrolo[3',4':3,4]pyrrolo[1,2-c]thiazol-5-yl]-benzimidamide hydrochloride. Colourless foam. M.p.: 182°–188° C. ISP-MS: 451 ([M+H]⁺, 100).

7.A)i) (5RS,5aSR,8aSR,8bRS)-4-[7-(Benzo[1,3]dioxol-5-ylmethyl)-6,8-dioxo-octahydro-pyrrolo[3',4':3,4]pyrrolo[1,2-c]thiazol-5-yl]-benzimidamide hydrochloride. Colourless solid. M.p.: 226°–229° C., dec. from 245° C. ISP-MS: 451 ([M+H]⁺, 100).

7.A)j) (1RS,3RS,3aSR,6aRS)-[5-(Benzo[1,3]dioxol-5-ylmethyl)-3-(4-carbamimidoyl-phenyl)-4,6-dioxo-octahydro-pyrrolo[3,4-c]pyrrol-1-yl]-methanesulfonic acid. Colourless solid. M.p.: 253°–256° C. ISP-MS: 471.3 ([M+H]⁺, 100).

7.A)k) (1RS,3RS,3aRS,6aRS)-[5-(Benzo[1,3]dioxol-5-ylmethyl)-3-(4-carbamimidoyl-phenyl)-4,6-dioxo-octahydro-pyrrolo[3,4-c]pyrrol-1-yl]-methanesulfonic acid. Colourless solid. M.p.: dec from 230° C. ISP-MS: 471 ([M+H]⁺, 100).

7.A)l) (3aS,4R,8S,8aS,8bR)-4-[2-(Benzo[1,3]dioxol-5-ylmethyl)-8-methyl-1,3-dioxo-decahydro-pyrrolo[3,4-a]pyrrolizin-4-yl]-benzimidamide hydrochloride. Colourless solid. M.p.: dec. from 220° C. ISP-MS: 447.2 ([M+H]⁺, 100).

7.A)m) (1RS,3SR,3aRS,6aSR)-3-(4-Carbamimidoyl-phenyl)-1-(2-methylsulfanyl-ethyl)-4,6-dioxo-5-phenyl-octahydro-pyrrolo[3,4-c]-pyrrole- 1-carboxylic acid. Colourless solid. ISP-MS: 454 ([M+H]⁺, 100).

7.A)n) (3aR,4R,7R,8aS,8bS)-4-(2-Benzyl-7-hydroxy-1,3-dioxo-decahydro-pyrrolo[3,4-a]pyrrolizin-4-yl)-benzimidamide hydrochloride. Colourless solid. ISP-MS: 405.1 ([M+H]⁺, 100).

7.A)o) (3aR,4S,7S,8aR,8bS)-4-(2-Benzyl-7-hydroxy-1,3-dioxo-decahydro-pyrrolo[3,4-a]pyrrolizin-4-yl)-benzimidamide hydrochloride. Colourless solid. ISP-MS: 405 ([M+H]⁺, 100).

7.A)p) 1:1 Mixture of methyl (R)-2-[(3aS,4S,8aR,8bR)- and -(3aR,4R,8aS,8bS)-4-(4-carbamimidoyl-phenyl)-1,3-dioxo-decahydro-pyrrolo[3,4-a]pyrrolizin-2-yl]-3-phenyl-propionate hydrochloride. Colourless solid. ISP-MS: 461.5 ([M+H]⁺, 100).

7.A)q) 1:1 Mixture of methyl (R)-2-[(3aR,4S,8aR,8bS)- and -(3aS,4R,8aS,8bR)-4-(4-carbamimidoyl-phenyl)-1,3-dioxo-decahydro-pyrrolo[3,4-a]pyrrolizin-2-yl]-3-phenyl-propionate hydrochloride. Colourless solid. M.p.: dec. from 182° C. ISP-MS: 461.5 ([M+H]⁺, 100).

7.A)r) (1RS,3SR,3aRS,6aSR)-4-[5-(Benzo[1,3]dioxol-5-ylmethyl)-3-hydroxymethyl-4,6-dioxo-octahydro-pyrrolo[3,4-c]pyrrol-1-yl]-benzimidamide hydrochloride. Colourless solid. M.p.: dec. from 197° C. ISP-MS: 423.4 ([M+H]⁺, 100).

7.A)s) (1RS,3RS,3aSR,6aRS)-4-[5-(Benzo[1,3]dioxol-5-ylmethyl)-3-hydroxymethyl-4,6-dioxo-octahydro-pyrrolo[3,4-c]pyrrol-1-yl]-benzimidamide hydrochloride. Colourless solid. ISP-MS: 423 ([M+H]⁺, 100).

7.A)t) (1S,2S,5R,5aS,8aR)-[7-Benzyl-5-(4-carbamimidoyl-phenyl)-2-(propen-2-yl)-6,8-dioxo-decahydro-pyrrolo[3,4-a]-pyrrolizin- 1-yl]-acetic acid. Colourless solid. ISP-MS: 487 ([M+H]⁺, 100).

Preparation of the corresponding starting materials:

7.B)a) (1RS,3SR,3aRS,6aSR)-4-(5-Benzyl-3-isobutyl-4,6-dioxo-octahydro-pyrrolo[3,4-c]pyrrol-1-yl)-benzonitrile was prepared analogously to Example 4.B) g) from 4-cyano-benzaldehyde, L-leucine and N-benzylmaleimide. Colourless prisms. M.p.: 152°–153° C. (methanol). EI-MS: 387 ([M]⁺, 4); 330 (100); 200 (6); 169 (48); 130 (7); 91 (57)

7.B)b) By methylating (1RS,3SR,3aRS,6aSR)-4-(5-benzyl-3-isobutyl-4,6-dioxo-octahydro-pyrrolo[3,4-c]pyrrol-1-yl)-benzonitrile according to Example 2.b) there was obtained (1RS,3SR,3aRS,6aSR)-4-(5-benzyl-3-isobutyl-2-methyl-4,6-dioxo-octahydro-pyrrolo[3,4-c]-pyrrol-1-yl)-benzonitrile. Colourless needles. M.p.: 173°–174° C. (methanol). ISP-MS: 402.5 ([M+H]⁺, 100).

7.B)c) (3aRS,4RS,8aSR,8bSR)-4-(2-Butyl-decahydro-1,3-dioxo-pyrrolo[3,4-a]pyrrolizin-4-yl)-benzonitrile was prepared analogously to Example 4.B)g) from 4-cyano-benzaldehyde, L-proline and N-butylmaleimide. Yellow oil. ¹H-NMR (DMSO-D6): 7.74 (d, ArH); 7.49 (d, ArH); 4.22 (d, 4-H).

7.B)d) (3aRS,4RS,9aSR,9bSR)-4-(2-Benzyl-1,3-dioxo-decahydro-pyrrolo[3,4-c]indolizin-4-yl)-benzonitrile was prepared analogously to Example 4.B)g) from 4-cyano-benzaldehyde, D,L-pipecolic acid and N-benzylmaleimide. Colourless prisms. M.p.: 153°–154° C. (methanol). ISP-MS: 386.4 ([M+H]⁺, 100).

7.B)e) By chromatography (hexane:ethyl acetate=1:1) of the crude product from Example 7.B)d) there was also obtained (3aRS, 4SR,9aRS,9bSR)-4-(2-benzyl-1,3-dioxo-decahydro-pyrrolo[3,4-c]-indolizin- 4-yl)-benzonitrile as colourless prisms. M.p.: 165°–167° C. (methanol). ISP-MS: 386.4 ([M+H]⁺, 100).

7.B)f) see Example 4.B)g)

7.B)g) (3aRS,4SR,8aRS,8bSR)-4-(2-Cyclohexylmethyl-1,3-dioxo-decahydro-pyrrolo[3,4-a]pyrrolizin-4-yl)-benzonitrile was prepared analogously to Example 4.B) g) from 4-cyano-benzaldehyde, L-proline and N-cyclohexylmethylmaleimide. Colourless crystals. M.p.: 119°–122° C. (ethyl acetate/hexane). ISP-MS: 378.4 ([M+H]⁺, 100).

7.B)h) (5RS,5aRS,8aSR,8bRS)-4-[7-(Benzo[1,3]dioxol-5-ylmethyl)-6,8-dioxo-octahydro-pyrrolo[3',4':3,4]pyrrolo[1,2-c]thiazol-5-yl]-benzonitrile was prepared analogously to Example 4.B)g) from 4-cyano-benzaldehyde, L-thioproline and N-piperonylmaleimide. Colourless needles. M.p.: 142°–143° C. (methanol). ISP-MS: 434.2 ([M+H]⁺, 100).

7.B)i) From the crude product of Example 7.B)h) there was also obtained by chromatography (hexane:ethyl acetate=1:1) (5RS, 5aSR,8aRS,8bRS)-4-[7-(benzo[1,3]

dioxol-5-ylmethyl)-6,8-dioxo-octahydro-pyrrolo[3', 4':3,4]pyrrolo[1,2-c]thiazol-5-yl]-benzonitrile. Colourless crystals. M.p.: 183°–184° C. (methanol). FAB-MS: 472 ([M+K]⁺, 25); 456 ([M+Na]⁺, 54); 434 ([M+H]⁺, 100).

7.B)j) 340 mg of (5RS,5aSR,8aRS,8bRS)-4-[7-(benzo[1,3]dioxol-5-ylmethyl)-6,8-dioxo-octahydro-pyrrolo[3',4':3,4]pyrrolo[1,2-c]thiazol-5-yl]-benzonitrile were stirred at room temperature for 4 hours with 300 mg of 3-chloroperbenzoic acid in dichloromethane. The crude product, (5RS,5aSR,8aRS,8bRS)-4-[7-(benzo[1,3]dioxol-5-ylmethyl)-2,2,6,8-tetraoxo-octahydro-pyrrolo[3',4':3,4]pyrrolo[1,2-c]thiazol-5-yl]-benzonitrile, was used directly as the starting compound in 7.A)j). ISP-MS: 466.1 ([M+H]⁺, 100).

7.B)k) 340 mg of (5RS,5aRS,8aSR,8bRS)-4-[7-(benzo[1,3]dioxol-5-ylmethyl)-6,8-dioxo-octahydro-pyrrolo[3',4':3,4]pyrrolo[1,2-c]thiazol-5-yl]-benzonitrile were stirred at room temperature for 4 hours with 300 mg of 3-chloroperbenzoic acid in dichloromethane. The crude product, (5RS,5aRS,8aSR,8bRS)-4-[7-(benzo[1,3]dioxol-5-ylmethyl)-2,2,6,8-tetraoxo-octahydro-pyrrolo[3',4':3,4]pyrrolo[1,2-c]thiazol-5-yl]-benzonitrile, was used directly as the starting compound in 7.A)k). ISP-MS: 466.1 ([M+H]⁺, 100).

7.B)l) (3aS,4R,8S,8aS,8bR)-4-[2-(Benzo[1,3]dioxol-5-ylmethyl)-8-methyl-1,3-dioxo-decahydro-pyrrolo[3,4-a]pyrrolizin-4-yl]-benzonitrile was obtained as a yellow foam analogously to Example 4.B)g) from 4-cyano-benzaldehyde, (2S,3S)-3-methylproline and N-piperonylmaleimide. ¹H-NMR (DMSO-D6): 7.85 (d, ArH); 7.63 (d, ArH); 4.24 (d, 4-H).

7.B)m) (1RS,3SR,3aRS,6aSR)-3-(4-Cyano-phenyl)-1-(2-methyl-sulfanyl-ethyl)-4,6-dioxo-5-phenyl-octahydro-pyrrolo[3,4-c]pyrrole-1-carboxylic acid, a yellow foam, which was recrystallized from ethanol, was obtained analogously to Example 1 from L-methionine, N-phenylmaleimide and 4-cyano-benzaldehyde. ISP-MS: 434.3 ([M–H]⁻, 100).

7.B)n) (3aR,4R,7R,8aS,8bS)-4-(2-Benzyl-7-hydroxy-1,3-dioxo-decahydro-pyrrolo[3,4-a]pyrrolizin-4-yl)-benzonitrile was prepared analogously to Example 4.B)g) from 4-cyano-benzaldehyde, (2S,3R)-hydroxyproline and N-benzylmaleimide. Yellow foam. ¹H-NMR (DMSO-D6): 7.65 (d, ArH); 7.40 (d, ArH); 4.79 (d, 4-H).

7.B)o) (3aR,4S,7S,8aR,8bS)-4-(2-Benzyl-7-hydroxy-1,3-dioxo-decahydro-pyrrolo[3,4-a]pyrrolizin-4-yl)-benzonitrile was obtained as a yellow foam analogously to Example 4.B)g) from 4-cyano-benzaldehyde, (2S,3S)-hydroxyproline and N-benzylmaleimide. ¹H-NMR (DMSO-D6): 7.62 (d, ArH); 7.40 (d, ArH); 4.35 (d, 4-H).

7.B)p) A 1:1 mixture of methyl (R)-2-[(3aS,4S,8aR,8bR)- and -(3aR,4R,8aS,8bS)-4-(4-cyano-phenyl)-1,3-dioxo-decahydro-pyrrolo[3,4-a]pyrrolizin-2-yl]-3-phenyl-propionate hydrochloride was obtained from methyl (2R)-2-(N-maleinimido)-3-phenyl-propionate, L-proline and 4-cyano-benzaldehyde. Yellow foam. ¹H-NMR (DMSO-D6): 7.85 (d, ArH); 7.82 (d, ArH); 7.61 (d, ArH); 7.46 (d, ArH); 3.70 (d, 4-H); 3.68 (d, 4-H).

7.B)q) A 1:1 mixture of methyl (R)-2-[(3aR,4S,8aR,8bS)- and -(3aS,4R,8aR,8bR)-4-(4-cyano-phenyl)-1,3-dioxo-decahydro-pyrrolo[3,4-a]pyrrolizin-2-yl]-3-phenyl-propionate hydrochloride was also isolated by chromatography of the crude product from Example 7.B)p). ¹H-NMR (DMSO-D6): 7.74 (d, ArH); 7.52 (d, ArH); 7.60 (d, ArH); 7.32 (d, ArH); 4.19 (d, 4-H); 4.08 (d, 4-H).

7.B)r) (1RS,3SR,3aRS,6aSR)-4-[5-(Benzo[1,3]dioxol-5-ylmethyl)-3-hydroxymethyl-4,6-dioxo-octahydro-pyrrolo[3,4-c]pyrrol-1-yl]-benzonitrile was prepared from N-piperonylmaleimide, 4-cyano-benzaldehyde and L-serine analogously to Example 4.B)g). ISP-MS: 406 ([M+H]⁺, 100).

7.B)s) (1RS,3RS,3aSR,6aRS)-4-[5-(Benzo[1,3]dioxol-5-ylmethyl)-3-hydroxymethyl-4,6-dioxo-octahydro-pyrrolo[3,4-c]pyrrol-1-yl]-benzonitrile was also isolated by chromatography of the crude product from Example 7.B)s). ISP-MS: 406 ([M+H]⁺, 100).

7.B)t) (1S,2S,5R,5aS,8aR)-[7-Benzyl-(5-cyano-phenyl)-2-(propen-2-yl)-6,8-dioxo-decahydro-pyrrolo[3,4-a]pyrrolizin-1-yl]-acetic acid was prepared from N-piperonylmaleimide, 4-cyano-benzaldehyde and kainic acid analogously to Example 4.B)g). Colourless solid. ¹H-NMR (DMSO-D6): 7.63 (d, ArH); 7.40 (d, ArH); 4.44 (d, 4-H).

EXAMPLE 8

150 mg of (5RS,5aSR,8aRS,8bRS)-4-[7-(Benzo[1,3]dioxol-5-ylmethyl)-6,8-dioxo-octahydro-pyrrolo[3',4':3,4]pyrrolo[1,2-c]thiazol-5-yl]-benzimidamide hydrochloride (Example 7.A)i) were dissolved in 20 ml of dichloromethane and treated with 170 mg of 3-chloroperbenzoic acid and stirred at room temperature for 4 hours. Thereafter, 130 mg of a colourless solid were filtered off and can be purified by chromatography on RP-18 with a water/methanol eluent. There were thus obtained 80 mg of (5RS,5aSR,8aRS,8bRS)-4-[7-(benzo[1,3]dioxol-5-ylmethyl)-2,2,6,8-tetraoxo-octahydro-pyrrolo-[3',4':3,4]pyrrolo[1,2-c]thiazol-5-yl]-benzimidamide hydrochloride. ISP-MS: 483.4 ([M+H]⁺, 100).

EXAMPLE 9

A mixture of L-proline (20 mmol), 4-nitrobenzaldehyde (20 mmol) and N-butylmaleimide (20 mmol) was heated to 80° C. in DMF (20 ml) for 24 hours. The solvent was removed in a high vacuum and the residue was separated chromatographically over silica gel (eluent hexane:ethyl acetate=1:1+1% triethylamine). (3aRS,4SR,8aRS,8bSR)-2-Butyl-4-(4-nitro-phenyl)-hexahydro-pyrrolo[3,4-a]pyrrolizine-1,3-dione was obtained in 32% yield as a yellow solid ($R_f$=0.35). This product in 50 ml of ethanol was treated with 200 mg of 10% palladium on charcoal and reduced under hydrogen within 8 hours. After filtration of the catalyst and removal of the solvent in a vacuum (3aRS,4SR,8aRS,8bSR)-4-(4-amino-phenyl)-2-butyl-hexahydro-pyrrolo[3,4-a]pyrrolizine-1,3-dione was obtained as a pale yellow oil ($R_f$=0.23). 120 mg of this crude product were treated with 80 mg of 3,5-dimethyl-pyrazolyl-1-carboximidamidinium nitrate in 20 ml of DMF and heated at 80° C. for 48 hours. After removing the solvent in a vacuum the material remaining was separated on a RP-18 chromatography column with a water/methanol gradient. (3aRS,4SR,8aRS, 8bSR)-N-[4-(2-Butyl-1,3-dioxo-decahydro-pyrrolo[3,4-a]pyrrolizin-4-yl)-phenyl]-guanidinium nitrate was obtained in 12% yield as a pale yellow oil. ISP-MS: 483.4 ([M+H]⁺, 100).

EXAMPLE 10

The following compounds were prepared in analogy to procedure 9:

10.a) (3aRS,4SR,8aRS,8bSR)-N-[4-(2-benzyl-1,3-dioxo-decahydro-pyrrolo[3,4-a]pyrrolizin-4-yl)-phenyl]-guanidinium nitrate as pale yellow crystals, ISP-MS: 404.5 ([M+H]$^+$, 100), from L-proline, 4-nitrobenzaldehyde and N-benzylmaleimide 10.b) (3aRS,4SR,8aRS,8bSR)-N-[4-[2-(benzo[1,3] dioxol-5-ylmethyl)-1,3-dioxo-decahydro-pyrrolo[3,4-a]pyrrolizin-4-yl]-phenyl]-guanidinium nitrate as yellow crystals, ISP-MS: 448.3 ([M+H]$^+$, 100), from L-proline, 4-nitrobenzaldehyde and N-piperonylmaleimide

EXAMPLE 11

The following compounds were prepared in analogy to procedure 4.B)f):

11.A)a) (3aRS,4SR,8aRS,8bSR)-2-Benzyl-4-(2,4-diamino-quinazolin-6-yl)-hexahydro-pyrrolo[3,4-a]pyrrolizine-1,3-dione as pale yellow crystals (ISP-MS: 429.3 ([M+H]$^+$, 100)) and (3aRS,4RS,8aSR,8bSR)-2-benzyl-4-(2,4-diamino-quinazolin-6-yl)-hexahydro-pyrrolo[3,4-a]pyrrolizine-1,3-dione as pale yellow crystals, (ISP-MS: 429.3 ([M+H]$^+$, 100)), from L-proline, 2,4-diamino-quinazoline-6-carbaldehyde and N-benzylmaleimide.

11.A)b) (3aRS,4SR,8aRS,8bSR)-2-Benzyl-4-(2,4-diamino-quinazolin-7-yl)-hexahydro-pyrrolo[3,4-a]pyrrolizine-1,3-dione as pale yellow crystals, ISP-MS: 429.3 ([M+H]$^+$, 100), from L-proline, 2,4-diamino-quinazoline-7-carbaldehyde and N-benzylmaleimide.

Preparation of the starting materials

11.B)a) 3,4-Diamino-quinazoline-6-carbaldehyde was prepared according to E. F. Elslager, J. Clarke, L. M. Werbel, D. F. Worth *J. Med. Chem.* Vol. 15, 827 (1972).

11.B)b) 2,4-Diamino-quinazoline-7-carbaldehyde was prepared in analogy to 11.B)a) from 2-amino-benzo-1,4-dinitrile according to J. Griffiths, B. Roozpeikar *J. Chem. Soc., Perkin Trans.* I 42 (1976).

EXAMPLE 12

5 g (1.5 mmol) of Fmoc-TGR resin according to H. Rink *Tetrahedron Lett.* 28, 3787 (1987) were shaken for 30 minutes, with a 20% solution of piperidine in DMF. Subsequently, the resin was washed with DMF. 1.19 g (3 mmol) of Fmoc-arginine, 950 mg (6 mmol) of 1-hydroxy-benzotriazole (HOBT—containing about 20% water), 570 mg of diisopropylcarbodiimide and DMF were added and the mixture was shaken for 1 hour. The resin was washed with DMF and shaken for 30 minutes with a 20% solution of piperidine in DMF. Thereafter, it was washed with DMF, isopropanol, water and methanol. Subsequently, the resin was distributed in equal portions in 30 reaction vessels, then 0.5 mmol of a carbonyl compound (a. paraformaldehyde, b. pivalaldehyde, c. benzaldehye, d. benzophenone and e. phenylpropionaldehyde) were added to in each case 6 of these vessels, whereafter to each 0.5 mmol of a maleimide (maleimide, N-methyl-, N-butyl-, N-cyclohexylmethyl-, N-phenyl- or N-benzyl-maleimide) was added such that each vessel contains a different pairing of carbonyl compound and maleimide. About 5 ml of a mixture of 150 ml of methanol and 8 ml of acetic acid were added to each vessel as the solvent and the batch was heated under reflux for 22 hours. After cooling the solvent was sucked off and the resin was washed in each case twice with dimethyl sulfoxide, isopropanol, water and isopropanol. The resin was then treated with in each case about 5 ml of a mixture of 40% trifluoroacetic acid, 50% dichloromethane, 5% water and 5% isopropanol and shaken for 2 hours. After filtration the 30 filtrate solutions were concentrated. 30 crude products were thus obtained as yellow oils. For mass spectroscopic and HPLC investigations about 0.5 mg of each oil was removed and taken up in 100 ml of water and 100 ml of acetonitrile. The remainder was dissolved in 0.5 ml of DMSO and the crude product having the highest inhibitory activity was determined using the thrombin test according to R. Lottenberg, J. A. Hall, J. W. Fenton, G. M. Jackson *Thrombosis Research* 28, 313 (1982) and the chromogenic substrate S-2238 at 405 nm wavelength.

The presence of the following 3,5-substituted 1-(3-guanidino-propyl)-4,6-dioxo-octahydro-pyrrolo[3,4-c]pyrrole-1-carboxamides could be detected with the aid of ion spray mass spectroscopy (ISP-MS):

a) 3-tert.Butyl-1-(3-guanidino-propyl)-4,6-dioxo-octahydro-pyrrolo[3,4-c]pyrrole-1-carboxamide;

b) 3-phenyl-1-(3-guanidino-propyl)-4,6-dioxo-octahydro-pyrrolo-[3,4-c]pyrrole-1-carboxamide;

c) 3-(2-phenyl-ethyl)-1-(3-guanidino-propyl)-4,6-dioxo-octahydro-pyrrolo[3,4-c]pyrrole-1-carboxamide;

d) 5-methyl-3-(2-phenyl-ethyl)-1-(3-guanidino-propyl)-4,6-dioxo-octahydro-pyrrolo[3,4-c]pyrrole-1-carboxamide;

e) 5-butyl-3-(2-phenyl-ethyl)-1-(3-guanidino-propyl)-4,6-dioxo-octahydro-pyrrolo[3,4-c]pyrrole-1-carboxamide;

f) 5-cyclohexylmethyl-3-(2-phenyl-ethyl)-1-(3-guanidino-propyl)-4,6-dioxo-octahydro-pyrrolo[3,4-c]pyrrole-1-carboxamide;

g) 5-benzyl-3-(2-phenyl-ethyl)-1-(3-guanidino-propyl)-4,6-dioxo-octahydro-pyrrolo[3,4-c]pyrrole-1-carboxamide;

h) 5-phenyl-3-(2-phenyl-ethyl)-1-(3-guanidino-propyl)-4,6-dioxo-octahydro-pyrrolo[3,4-c]pyrrole-1-carboxamide;

i) 5-butyl-3,3-diphenyl-1-(3-guanidino-propyl)-4,6-dioxo-octahydro-pyrrolo[3,4-c]pyrrole-1-carboxamide;

j) 5-butyl-3-phenyl-1-(3-guanidino-propyl)-4,6-dioxo-octahydro-pyrrolo[3,4-c]pyrrole-1-carboxamide;

k) 5-cyclohexylmethyl-3-phenyl-1-(3-guanidino-propyl)-4,6-dioxo-octahydro-pyrrolo[3,4-c]pyrrole-1-carboxamide;

l) 5-benzyl-3-phenyl-1-(3-guanidino-propyl)-4,6-dioxo-octahydro-pyrrolo[3,4-c]pyrrole-1-carboxamide;

m) 3,5-diphenyl-1-(3-guanidino-propyl)-4,6-dioxo-octahydro-pyrrolo[3,4-c]pyrrole-1-carboxamide;

n) 5-butyl-3-tert.butyl-1-(3-guanidino-propyl)-4,6-dioxo-octahydro-pyrrolo[3,4-c]pyrrole-1-carboxamide;

o) 5-butyl-1-(3-guanidino-propyl)-4,6-dioxo-octahydro-pyrrolo-[3,4-c]pyrrole-1-carboxamide; and, respectively, p) 1-(3-guanidino-propyl)-4,6-dioxo-octahydro-5-phenyl-pyrrolo[3,4-c]pyrrole-1-carboxamide.

Of the named cycloadducts the crude product which contained 1-(3-guanidino-propyl)-4,6-dioxo-octahydro-3,5-diphenyl-pyrrolo[3,4-c]pyrrole-1-carboxamide showed the greatest inhibitory activity in the thrombin test.

EXAMPLE 13

80 mg aliquots of TGA resin according to E. Bayer, W. Rapp *Chem. Pept. Prot.* 3, 3 (1986), each derivatized with a FmOc-protected amino acid (glycine, L-alanine, L-valine, L-isolucine, L-methionine, L-proline, corresponding to in each case about 0.016 mmol) were shaken for 30 minutes in 6 reaction vessels with a 20% solution of piperidine in DMF and thereafter washed with DMF. Subsequently, each of the 6 resin portions were distributed equally in 5 vessels, whereafter 0.16 mmol of 4-cyano-benzaldehyde, 0.16 mmol of triethylamine and 0.24 mmol of silver acetate were added to each of these 30 vessels. Thereto there was added 0.16 mmol of maleimide (N-methyl-, N-butyl-, N-cyclohexylmethyl-, N-phenyl- or N-benzyl-maleimide) such that each vessel contains a different pairing from one amino acid resin and one maleimide. About 3 ml of acetonitrile were added as the solvent to each vessel and the mixture was shaken at room temperature for 1 week. After cooling the solvent was sucked off and the resin was washed twice each time with acetonitrile, isopropanol, water and isopropanol. The 30 resin portions were dried in a high vacuum and thereafter treated at 0° C. with 8 ml of a 5:1 mixture of chloroform and methanol saturated with dry hydrogen chloride and left to stand at 4° C. for 48 hours. Thereafter, the solvent was removed at 30° C. in a vacuum. After adding 8 ml of an ammonia-saturated methanol solution the mixture was heated at 65° C. for 3 hours. After filtration the 30 filtrate solutions were concentrated. There were thus obtained 30 crude products as colourless to yellow solids. For mass spectroscopic and HPLC investigations about 0.5 mg of each solid was removed and taken up in 100 ml of water and 100 ml of acetonitrile. The remainder was dissolved in 0.5 ml of DMSO and the crude product having the highest inhibitory activity was determined according to Example 12.

The presence of the following 1,5-substituted 3-(4-carbamimidoyl-phenyl)-4,6-dioxo-octahydro-pyrrolo[3,4-c]pyrrol-1-carboxylic acids could be detected with the aid of ion spray mass spectroscopy (ISP-MS):

a) 5-Methyl-3-(4-carbamimidoyl-phenyl)-4,6-dioxo-octahydro-pyrrolo[3,4-c]pyrrole-1-carboxylic acid;
b) 1,5-dimethyl-3-(4-carbamimidoyl-phenyl)-4,6-dioxo-octahydro-pyrrolo[3,4-c]pyrrole-1-carboxylic acid;
c) 5-methyl-1-(2-propyl)-3-(4-carbamimidoyl-phenyl)-4,6-dioxo-octahydro-pyrrolo[3,4-c]pyrrole-1-carboxylic acid;
d) 1-(2-butyl)-5-methyl-3-(4-carbamimidoyl-phenyl)-4,6-dioxo-octahydro-pyrrolo[3,4-c]pyrrole-1-carboxylic acid;
e) 5-methyl-1-(2-methylsulfanyl-ethyl)-3-(4-carbamimidoyl-phenyl)-4,6-dioxo-octahydro-pyrrolo[3,4-c]pyrrole-1-carboxylic acid;
f) 5-butyl-3-(4-carbamimidoyl-phenyl)-4,6-dioxo-octahydro-pyrrolo[3,4-c]pyrrole-1-carboxylic acid;
g) 5-butyl-1-methyl-3-(4-carbamimidoyl-phenyl)-4,6-dioxo-octahydro-pyrrolo[3,4-c]pyrrole-1-carboxylic acid;
h) 5-butyl-1-(2-propyl)-3-(4-carbamimidoyl-phenyl)-4,6-dioxo-octahydro-pyrrolo[3,4-c]pyrrole-1-carboxylic acid;
i) 5-butyl-1-(2-butyl)-3-(4-carbamimidoyl-phenyl)-4,6-dioxo-octahydro-pyrrolo[3,4-c]pyrrole-1-carboxylic acid;
j) 5-butyl-1-(2-methylsulfanyl-ethyl)-3-(4-carbamimidoyl-phenyl)-4,6-dioxo-octahydro-pyrrolo[3,4-c]pyrrole-1-carboxylic acid;
k) 5-cyclohexylmethyl-3-(4-carbamimidoyl-phenyl)-4,6-dioxo-octahydro-pyrrolo[3,4-c]pyrrole-1-carboxylic acid;
l) 5-cyclohexylmethyl-1-(2-propyl)-3-(4-carbamimidoyl-phenyl)-4,6-dioxo-octahydro-pyrrolo[3,4-c]pyrrole-1-carboxylic acid;
m) 1-(2-butyl)-5-cyclohexylmethyl-3-(4-carbamimidoyl-phenyl)-4,6-dioxo-octahydro-pyrrolo[3,4-c]pyrrole-1-carboxylic acid;
n) 5-cyclohexylmethyl-1-(2-methylsulfanyl-ethyl)-3-(4-carbamimidoyl-phenyl)-4,6-dioxo-octahydro-pyrrolo[3,4-c]pyrrole-1-carboxylic acid;
o) 5-phenyl-3-(4-carbamimidoyl-phenyl)-4,6-dioxo-octahydro-pyrrolo[3,4-c]pyrrole-1-carboxylic acid;
p) 1-methyl-5-phenyl-3-(4-carbamimidoyl-phenyl)-4,6-dioxo-octahydro-pyrrolo[3,4-c]pyrrole-1-carboxylic acid;
q) 5-phenyl-1-(2-propyl)-3-(4-carbamimidoyl-phenyl)-4,6-dioxo-octahydro-pyrrolo[3,4-c]pyrrole-1-carboxylic acid;
r) 1-(2-butyl)-5-phenyl-3-(4-carbamimidoyl-phenyl)-4,6-dioxo-octahydro-pyrrolo[3,4-c]pyrrole-1-carboxylic acid;
s) 1-(2-methylsulfanyl-ethyl)-5-phenyl-3-(4-carbamimidoyl-phenyl)-4,6-dioxo-octahydro-pyrrolo[3,4-c]pyrrole-1-carboxylic acid;
t) 5-benzyl-3-(4-carbamimidoyl-phenyl)-4,6-dioxo-octahydro-pyrrolo[3,4-c]pyrrole-1-carboxylic acid;
u) 5-benzyl-1-methyl-3-(4-carbamimidoyl-phenyl)-4,6-dioxo-octahydro-pyrrolo[3,4-c]pyrrole-1-carboxylic acid;
v) 5-benzyl-1-(2-propyl)-3-(4-carbamimidoyl-phenyl)-4,6-dioxo-octahydro-pyrrolo[3,4-c]pyrrole-1-carboxylic acid;
w) 5-benzyl-1-(2-butyl)-3-(4-carbamimidoyl-phenyl)-4,6-dioxo-octahydro-pyrrolo[3,4-c]pyrrole-1-carboxylic acid; and, respectively,
x) 5-benzyl-3-(4-carbamimidoyl-phenyl)-1-(2-methylsulfanyl-ethyl)-4,6-dioxo-octahydro-pyrrolo[3,4-c]pyrrole-1-carboxylic acid.

Likewise, the following 2-substituted[4-(4-carbamimidoyl-phenyl)-1,3-dioxo-decahydro-pyrrolo[3,4-a]pyrrolizin-8a-yl]-carboxylic acids could be detected:

a') [2-Methyl-4-(4-carbamimidoyl-phenyl)-1,3-dioxo-decahydro-pyrrolo[3,4-a]pyrrolizin-8a-yl]-carboxylic acid;
b') [2-butyl-4-(4-carbamimidoyl-phenyl)-1,3-dioxo-decahydro-pyrrolo[3,4-a]pyrrolizin-8a-yl]-carboxylic acid;
c') [2-cyclohexylmethyl-4-(4-carbamimidoyl-phenyl)-1,3-dioxo-decahydro-pyrrolo[3,4-a]pyrrolizin-8a-yl]-carboxylic acid;
d') [2-phenyl-4-(4-carbamimidoyl-phenyl)-1,3-dioxo-decahydro-pyrrolo[3,4-a]pyrrolizin-8a-yl]-carboxylic acid; and, respectively,
e') [2-benzyl-4-(4-carbamimidoyl-phenyl)-1,3-dioxo-decahydro-pyrrolo[3,4-a]pyrrolizin-8a-yl]-carboxylic acid.

Of the named cycloadducts the crude product which contained 3-(4-carbamimidoyl-phenyl)-5-cyclohexylmethyl-1-(2-methylsulfanyl-ethyl)-4,6-dioxo-octahydro-pyrrolo[3,4-c]pyrrole-1-carboxylic acid showed the greatest inhibitory activity in the thrombin test.

EXAMPLE 14

20 g of MBHA resin (corresponding to 22 mmol) were shaken at room temperature for 2 hours with 10 g of 3-bromopropionic acid and 7.8 ml of diisopropylcarbodiimide in dimethyformamide. The resin was washed with with dimethylformamide and dimethyl sulfoxide. 1 g aliquots of the resin were thereafter treated with in each case 10 mmol of an amino acid (glycine, L-alanine, L-valine, L-phenylalanine, L-lucine and L-serine) and 100 mg of potassium iodide and 8 ml of dimethyl sulfoxide were added as the solvent and thereafter the mixture was shaken at room temperature for 48 hours. Each of these resins was divided into 5 equal parts and 1 mmol of 4-cyano-benzaldehyde as well as in each case 1 mmol of a maleimide (N-methyl-, N-butyl-, N-phenyl-, N-benzyl-maleimide or N-phenethyl-maleimide) in 7 ml of dimethylformamide were added and thereafter the mixture was held at 95° C. for 60 hours, with the resin being intermixed with a light stream of nitrogen. Thereafter, the mixture was suction filtered and the resin was washed with dimethylformamide, isopropanol, water, isopropanol and methylene chloride. The 30 resin portions were dried in a high vacuum for 48 hours and thereafter treated at 0° C. with 8 ml of a 5:1 mixture of chloroform and methanol saturated with dry hydrogen chloride and left to stand at 4° C. for 24 hours. Thereafter, the solvent was removed at 30° C. in a vacuum. After adding 8 ml of an ammonia-saturated methanol solution the mixture was heated at 65° C. for 4 hours. After filtration the 30 filtrate solutions were concentrated. There were thus obtained 30 crude products as colourless to yellow solids. For mass spectroscopic and HPLC investigations about 0.5 mg of each solid was removed and taken up in 100 μl of water and 100 μl of acetonitrile. The remainder was dissolved in 0.5 ml of DMSO and the crude product having the highest inhibitory activity was determined according to Example 12.

The presence of the following 3,5-substituted 1-(4-carbamimidoyl-phenyl)-2-(2-carbamoyl-ethyl)-4,6-dioxo-octahydro-pyrrolo[3,4-c]pyrrole-3-carboxylic acids could be detected with the aid of ion spray mass spectroscopy (ISP-MS):

a) 5-Methyl-1-(4-carbamimidoyl-phenyl)-2-(2-carbamoyl-ethyl)-4,6-dioxo-octahydro-pyrrolo[3,4-c]pyrrole-3-carboxylic acid;

b) 3,5-dimethyl-1-(4-carbamimidoyl-phenyl)-2-(2-carbamoyl-ethyl)-4,6-dioxo-octahydro-pyrrolo[3,4-c]pyrrole-3-carboxylic acid;

c) 5-methyl-3-(prop-2-yl)-1-(4-carbamimidoyl-phenyl)-2-(2-carbamoyl-ethyl)-4,6-dioxo-octahydro-pyrrolo[3,4-c]pyrrole-3-carboxylic acid;

d) 5-methyl-3-(2-methyl-propyl)-1-(4-carbamimidoyl-phenyl)-2-(2-carbamoyl-ethyl)-4,6-dioxo-octahydro-pyrrolo[3,4-c]pyrrole-3-carboxylic acid;

e) 3-hydroxymethyl-5-methyl-1-(4-carbamimidoyl-phenyl)-2-(2-carbamoyl-ethyl)-4,6-dioxo-octahydro-pyrrolo[3,4-c]pyrrole-3-carboxylic acid;

f) 3-benzyl-5-methyl-1-(4-carbamimidoyl-phenyl)-2-(2-carbamoyl-ethyl)-4,6-dioxo-octahydro-pyrrolo[3,4-c]pyrrole-3-carboxylic acid;

g) 5-butyl-1-(4-carbamimidoyl-phenyl)-2-(2-carbamoyl-ethyl)-4,6-dioxo-octahydro-pyrrolo[3,4-c]pyrrole-3-carboxylic acid;

h) 5-butyl-3-methyl-1-(4-carbamimidoyl-phenyl)-2-(2-carbamoyl-ethyl)-4,6-dioxo-octahydro-pyrrolo[3,4-c]pyrrole-3-carboxylic acid;

i) 5-butyl-3-(prop-2-yl)-1-(4-carbamimidoyl-phenyl)-2-(2-carbamoyl-ethyl)-4,6-dioxo-octahydro-pyrrolo[3,4-c]pyrrole-3-carboxylic acid;

j) 5-butyl-3-(2-methyl-propyl)-1-(4-carbamimidoyl-phenyl)-2-(2-carbamoyl-ethyl)-4,6-dioxo-octahydro-pyrrolo[3,4-c]pyrrole-3-carboxylic acid;

k) 5-butyl-3-hydroxymethyl-1-(4-carbamimidoyl-phenyl)-2-(2-carbamoyl-ethyl)-4,6-dioxo-octahydro-pyrrolo[3,4-c]pyrrole-3-carboxylic acid;

l) 3-benzyl-5-butyl-1-(4-carbamimidoyl-phenyl)-2-(2-carbamoyl-ethyl)-4,6-dioxo-octahydro-pyrrolo[3,4-c]pyrrole-3-carboxylic acid;

m) 3-methyl-5-phenyl-1-(4-carbamimidoyl-phenyl)-2-(2-carbamoyl-ethyl)- 4,6-dioxo-octahydro-pyrrolo[3,4-c]pyrrole-3-carboxylic acid;

n) 5-phenyl-3-(prop-2-yl)-1-(4-carbamimidoyl-phenyl)-2-(2-carbamoyl-ethyl)-4,6-dioxo-octahydro-pyrrolo[3,4-c]pyrrole-3-carboxylic acid;

o) 3-(2-methyl-propyl)-5-phenyl-1-(4-carbamimidoyl-phenyl)-2-(2-carbamoyl-ethyl)-4,6-dioxo-octahydro-pyrrolo[3,4-c]pyrrole-3-carboxylic acid;

p) 3-hydroxymethyl-5-phenyl-1-(4-carbamimidoyl-phenyl)-2-(2-carbamoyl-ethyl)-4,6-dioxo-octahydro-pyrrolo[3,4-c]pyrrole-3-carboxylic acid;

q) 3-benzyl-5-phenyl-1-(4-carbamimidoyl-phenyl)-2-(2-carbamoyl-ethyl)-4,6-dioxo-octahydro-pyrrolo[3,4-c]pyrrole-3-carboxylic acid;

r) 5-benzyl-3-methyl-1-(4-carbamimidoyl-phenyl)-2-(2-carbamoyl-ethyl)-4,6-dioxo-octahydro-pyrrolo[3,4-c]pyrrole-3-carboxylic acid;

s) 5-benzyl-3-(2-methyl-propyl)-1-(4-carbamimidoyl-phenyl)-2-(2-carbamoyl-ethyl)-4,6-dioxo-octahydro-pyrrolo[3,4-c]pyrrole-3-carboxylic acid;

t) 5-benzyl-3-hydroxymethyl-1-(4-carbamimidoyl-phenyl)-2-(2-carbamoyl-ethyl)-4,6-dioxo-octahydro-pyrrolo[3,4-c]pyrrole-3-carboxylic acid;

u) 3,5-dibenzyl-1-(4-carbamimidoyl-phenyl)-2-(2-carbamoyl-ethyl)-4,6-dioxo-octahydro-pyrrolo[3,4-c]pyrrole-3-carboxylic acid;

v) 5-(2-phenyl-ethyl)-1-(4-carbamimidoyl-phenyl)-2-(2-carbamoyl-ethyl)-4,6-dioxo-octahydro-pyrrolo[3,4-c]pyrrole-3-carboxylic acid;

w) 5-(2-phenyl-ethyl)-3-(prop-2-yl)-1-(4-carbamimidoyl-phenyl)-2-(2-carbamoyl-ethyl)-4,6-dioxo-octahydro-pyrrolo[3,4-c]pyrrole-3-carboxylic acid;

x) 3-(2-methyl-propyl)-5-(2-phenyl-ethyl)-1-(4-carbamimidoyl-phenyl)-2-(2-carbamoyl-ethyl)-4,6-dioxo-octahydro-pyrrolo[3,4-c]-pyrrole-3-carboxylic acid;

y) 3-hydroxymethyl-5-(2-phenyl-ethyl)-1-(4-carbamimidoyl-phenyl)-2-(2-carbamoyl-ethyl)-4,6-dioxo-octahydro-pyrrolo[3,4-c]-pyrrole-3-carboxylic acid; and, respectively, z) 3-benzyl-1-(4-carbamimidoyl-phenyl)-2-(2-carbamoyl-ethyl)-4,6-dioxo-octahydro-5-(2-phenyl-ethyl)-pyrrolo[3,4-c]pyrrole-3-carboxylic acid, with 1-(4-carbamimidoyl-phenyl)-2-(2-carbamoyl-ethyl)-3-hydroxymethyl-4,6-dioxo-octahydro-5-phenyl-pyrrolo-[3,4-c]pyrrole-3-carboxylic acid showing the highest inhibitory activity.

EXAMPLE 15

1 g aliquots of MBHA resin (corresponding to 1.1 mmol) were shaken at room temperature for 3 hours with in each case 3.3 mmol of a Fmoc-protected amino acid (glycine, L-leucine, L-phenylalanine orD-phenylalanine) and 3.3 mmol of diisopropylcarbodiimide in 7 ml of dimethylformamide. The resin was washed with dimethylformamide and dimethyl sulfoxide and subsequently shaken for 30 minutes in 4 reaction vessels with a 20% solution of piperidine in DMF and then washed with DMF. 5.5 mmol of maleic anhydride in 10 ml of dichloromethane were added to each of the 4 reaction batches and the mixtures were shaken at room temperature over 60 hours. After suction filtration of the reaction solutions and washing with dichloro-methane 2 g of sodium acetate and 10 ml of acetic anhydride were added to each solution and the mixtures were heated at 100° C. for 1 hour. Subsequently, suction filtration was carried out followed by washing 4 times with water, a 2N sodium carbonate solution, water, isopropanol and dichloromethane. Each of the 4 reaction batches was partitioned in 5 vessels and to each was added 1 mmol of an amino acid (glycine, L-alanine, L-proline, L-hydroxyproline and L-serine) as well as 1 mmol of 4-cyano-benzaldehyde in 3 ml of DMF. The reaction was then carried out at 60° C. for 30 hours and at 100° C. for 5 hours. Thereafter, the mixture was suction filtered and the resin was washed with dimethylformamide, isopropanol, water, isopropanol and methylene chloride. The 20 resin portions were dried in a high vacuum for 48 hours and thereafter treated at 0° C. with 8 ml of a 5:1 mixture of chloroform and methanol saturated with dry hydrogen chloride and left to stand at 4° C. for 24 hours. Thereafter, the solvent was removed at 30° C. in a vacuum. After adding 8 ml of an ammonia-saturated methanol solution the mixture was heated at 65° C. for 4 hours. After filtration the 20 filtrate solutions were concentrated. There were thus obtained 20 crude products as colourless to yellow solids. The crude products were dissolved in 0.5 ml of DMSO and the crude product having the highest inhibitory activity was determined according to Example 12. The crude product which contains 2-[4-(4-carbamimidoyl-phenyl)-1,3-dioxo-decahydro-pyrrolo[3,4-a]pyrrolizin-2-yl]-3-phenyl-propionic acid according to ion spray mass spectroscopy (ISP-MS: 446.2 [M+H]$^+$) shows the highest inhibitory activity in the thrombin test.

EXAMPLE 16

592 mg (3 mmol) of O-benzylserine, 393 mg (3 mmol) of 4-cyano-benzaldehyde and 697 mg (3 mmol) of N-(4-nitro-benzyl)-maleimide in 25 ml of DMF were heated at 110° C. for 5 hours. After cooling the solvent was removed in a vacuum. The crude product was filtered over silica gel with hexane/ethyl acetate and the solvent was removed. Thereafter, the residue was dissolved in a methanol/chloroform (1:5) mixture and dry hydrogen chloride was introduced while cooling with ice. After standing at 4° C. for 14 hours the solution was treated with ether and the colourless precipitate was filtered off and thereafter boiled at reflux for 3 hours with a methanol solution saturated with ammonia. The solvent was removed in a vacuum. The thus-obtained crude product was treated with 3 ml of 1N hydrochloric acid and again evaporated. The yellowish residue was separated over a RP-18 chromatography column with a water/methanol gradient. 67 mg of (1RS,3RS,3aSR,6aRS)-4-[3-(benzyloxy-methyl)-5-(4-nitro-benzyl)-4,6-dioxo-octahydro-pyrrolo[3,4-c]pyrrol-1-yl]-benzimidamide hydrochloride were isolated as a yellowish powder. ISP-MS: 514 ([M+H]$^+$, 100).

EXAMPLE 17

From (1RS,3RS,3aSR,6aRS)-4-[3-(benzyloxy-methyl)-5-(4-nitro-benzyl)-4,6-dioxo-octahydro-pyrrolo[3,4-c]pyrrol-1-yl]-benzimidamide hydrochloride by hydrogenation with 10% Pd on charcoal in glacial acetic acid at room temperature there was obtained (1RS,3RS,3aSR,6aRS)-4-[5-(4-amino-benzyl)-3-(benzyloxy-methyl)-4,6-dioxo-octahydro-pyrrolo[3,4-c]pyrrol-1-yl]-benzimidamide hydrochloride as a yellowish powder. ISP MS: 484 ([M+H]$^+$, 100).

EXAMPLE 18

592 mg (3 mmol) of O-benzylserine, 393 mg (3 mmol) of 4-cyano-benzaldehyde, 697 mg (3 mmol) of N-(4-nitro-benzyl)-maleimide and 10 drops of acetic acid in 25 ml of methanol were heated under reflux for 3 days. After cooling the solvent was removed in a vacuum and the crude product was triturated with ether. The yellow crystalline product was filtered off and washed with ether. Thereafter, it was dissolved in a methanol/chloroform (1:5) mixture and dry hydrogen chloride was introduced while cooling with ice. After standing at 4° C. for 14 hours the solution was treated with ether and the colourless precipitate was filtered off and thereafter boiled at reflux for 3 hours with a methanol solution saturated with ammonia. The solvent was removed in a vacuum. The thus-obtained crude product was treated with 3 ml of 1N hydrochloric acid and again evaporated. The yellowish residue was separated over a RP-18 chromatography column with a water/methanol gradient. 355 mg of (1RS,3RS,3aSR,6aRS)-1-(benzyloxy-methyl)-3-(4-carbamimidoyl-phenyl)-5-(4-nitro-benzyl)-4,6-dioxo-octahydro-pyrrolo[3,4-c]pyrrole-1-carboxylic acid hydrochloride were isolated as a yellowish powder. ISP-MS: 558 ([M+H]$^+$, 100).

EXAMPLE 19

From (1RS,3RS,3aSR,6aRS)-1-(benzyloxy-methyl)-3-(4-carbamimidoyl-phenyl)-5-(4-nitro-benzyl)-4,6-dioxo-octahydro-pyrrolo[3,4-c]pyrrole-1-carboxylic acid hydrochloride by hydrogenation with 10% palladium on charcoal in glacial acetic acid at room temperature there was obtained (1RS,3RS,3aSR,6aRS)-5-(4-amino-benzyl)-1-(benzyloxy-methyl)-3-(4-carbamimidoyl-phenyl)-4,6-dioxo-octahydro-pyrrolo[3,4-c]pyrrole-1-carboxylic acid hydrochloride as a yellowish powder. ISP-MS: 528 ([M+H]$^+$, 100).

A compound of Formula I, a solvate or salt thereof can be used in a manner known per se as the active ingredient for the production of pharmaceutical preparations, e.g. of tablets and capsules of the following composition:

| Example A | |
|---|---|
| | Per tablet |
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

| Example B | |
|---|---|
| | Per capsule |
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

We claim:

1. An octahydro-1,3-dioxo-pyrrolo[3,4-c]pyrrole compound having the formula

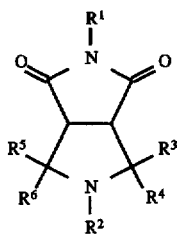

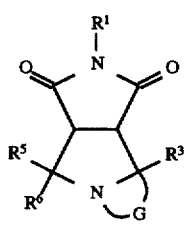

wherein

R¹ is selected from the group consisting of H, lower alkyl, aryl, heteroaryl, cycloalkyl and lower-alkyl which is substituted with a group $R^{10}$ and optionally a group $R^{11}$ or with a group $R^{11}$ and optionally a group $R^{10}$;

R² is selected from the group consisting of lower-alkanoyl, H, lower-alkyl, aryl, heteroaryl, cycloalkyl and lower-alkyl which is substituted with a group $R^{10}$ and optionally a group $R^{11}$ or with a group $R^{11}$ and optionally a group $R^{10}$;

$R^{10}$ is $CONH_2$ or COO-lower-alkyl;

$R^{11}$ is aryl, heteroaryl or cycloalkyl;

R³ is selected from the group consisting of H, COOH, $CONH_2$, COO-lower-alkyl, CONH-lower-alkyl and CON(lower-alkyl)₂; and R⁴, R⁵ and R⁶ are each independently selected from the group consisting of H, lower alkyl, aryl, aralkyl or cycloalkyl, or R⁴ and optionally R⁵ or R⁶ are a group $R^{40}$, or R⁵ or R⁶ and optionally R⁴ are a group $R^{40}$;

$R^{40}$ is heteroaryl, or lower-alkyl substituted with OH, $SO_2H$, $SO_3H$, guanidino, aryl-lower-alkoxy or lower-alkyl-(O or S); or R² and R⁴ together form a group G, wherein G is a tri- or tetramethylene group $(CH_2)_3$ or $(CH_2)_4$ wherein one methylene group may be replaced by S, SO or $SO_2$, or may be substituted with OH, lower-alkyl, lower-alkenyl or carboxy-lower-alkyl, or wherein one methylene group may be substituted with lower-alkenyl and another methylene group may be substituted with carboxy-lower-alkyl; wherein lower alkyl and alkanoyl are a straight-chain or branched group having, from 1 to 6 carbon atoms; cycloalkyl is a saturated group having from 3 to 7 carbon atoms; and heteroaryl is an aromatic group having from 5 to 10 members, containing at least one N atom and which further can be substituted by at least one $NH_2$ group; with the proviso that at least one of R¹, R², R⁴, R⁵ and R⁶ is a group substituted with amino, amidino, guanidino or N-hydroxyamidino; and hydrates or solvates and physiologically usable salts thereof.

2. The compounds of claim 1, wherein R² is lower-alkanoyl, H, lower-alkyl, aryl, heteroaryl, cycloalkyl or lower-alkyl which is substituted with a group $R^{10}$ and optionally a group $R^{11}$ or with a group $R^{11}$ and optionally a group $R^{10}$.

3. The compounds of claim 2, wherein R² is selected from the group consisting of H; lower alkyl; lower-alkanoyl; and lower-alkyl substituted with $CONH_2$.

4. The compound of claim 1, wherein R² and R⁴ together form group G, and form a compound having the formula wherein group G comprises a tri- or tetramethylene $(CH_2)_3$ or $(CH_2)_4$, wherein one methylene group may be replaced by S, SO or $SO_2$, or may be substituted with OH, lower-alkyl, carboxy-lower-alkyl or lower-alkenyl, or one methylene group may be substituted with lower-alkenyl and another methylene group may be substituted with lower-alkyl-COOH; and one or more of groups R¹, R⁴, R⁵, and R⁶ is a group substituted with amino, amidino, guanidino or N-hydroxyamidino; and hydrates or solvates and physiologically usable salts thereof.

5. The compound of claim 3 wherein R² is selected from H, methyl, carbamoylethyl and acetyl.

6. The compound of claim 5, wherein R¹ is selected from the group consisting of H, lower alkyl, aryl and lower-alkyl substituted with $CONH_2$ or COO-lower-alkyl, aryl or cycloalkyl.

7. The compound of claim 4, wherein R¹ is selected from the group consisting of H; $CH_3$; benzyl; butyl; phenyl; phenethyl; cyclohexylmethyl; and benzyl substituted with nitro, amino or methylenedioxy.

8. The compound of claim 7 wherein R¹ is benzo[1,3] dioxol-5-ylmethyl.

9. The compound of claim 7, wherein R³ is selected from the group consisting of H, COOH or $CONH_2$.

10. The compound of claim 9, wherein R⁴ is selected from the group consisting of H, lower alkyl, aryl, aralkyl and lower-alkyl substituted with OH, $SO_2H$, guanidino, aralkoxy or lower-alkylthio.

11. The compound of claim 10 wherein R⁴ is selected from the group consisting of methyl, isopropyl, isobutyl, 2-butyl, tert.-butyl, phenyl, benzyl, $CH_2OH$, $CH_2SO_2H$, guanidinopropyl, benzyloxymethyl and $(CH_2)_2SCH_3$.

12. The compound of claim 11, wherein R⁵ and R⁶ are each independently selected from the group consisting of H, lower-alkyl, aryl and aralkyl.

13. The compound of claim 12 wherein R⁵ and R⁶ are each independently selected from the group consisting of H, methyl, tert.-butyl, phenyl, phenethyl, amidinophenyl and hydroxyamidinophenyl.

14. The compound of claim 13 selected from the group consisting of:

(1RS,3SR,3aRS,6aSR)-4-(5-Benzyl-2,3-dimethyl-4,6-dioxo-octahydro-pyrrolo[3,4-c]pyrrol-1-yl)-benzimidamide;

(1RS,3RS,3aSR,6aRS)-1-(Benzyloxy-methyl)-3-(4-carbamimidoyl-phenyl)-5-(4-nitro-benzyl)-4,6-dioxo-octahydro-pyrrolo[3,4-c]pyrrole-1-carboxylic acid; and (1RS,3RS,3aS R,6aRS)-5-(4-amino-benzyl)-1-(benzyloxy-methyl)-3-(4-carbamimidoyl-phenyl)-4,6-dioxo-octahydro-pyrrolo[3,4-c]-pyrrole-1-carboxylic acid.

15. The compound of claim 13 selected from the group consisting of:

(1RS,3SR,3aRS,6aSR)-5-Benzyl-1-(3-guanidino-propyl)-4,6-dioxo-octahydro-3-phenyl-pyrrolo[3,4-c]pyrrole-1-carboxylic acid;

(1RS,3aSR,6aRS)-4-(5-benzyl-2,3,3-trimethyl-4,6-dioxo-octahydro-pyrrolo[3,4-c]pyrrol-1-ylmethyl)-benzimidamide;

(3 aRS,4RS,6aSR)-4-[4-(amino-hydroxyimino-methyl)-benzyl]-2-benzyl-5,6,6-trimethyl-tetrahydro-pyrrolo[3,4-c]pyrrole-1,3-dione;

(1RS,3SR,3aRS,6aSR)-4-(5-benzyl-3-methyl-4,6-dioxo-octahydro-pyrrolo[3,4-c]pyrrol-1-yl)-benzimidamide;

(1RS,3SR,3aRS,6aSR)-4-(2-acetyl-5-benzyl-3-methyl-4,6-dioxo-octahydro-pyrrolo[3,4-c]pyrrol-1-yl)-benzimidamide;

(1RS,3SR,3aRS,6aSR)-4-(5-butyl-2,3-dimethyl-4,6-dioxo-octahydro-pyrrolo[3,4-c]pyrrol-1-yl)-benzimidamide;

(1RS,3SR,3aRS,6aSR)-4-(2-acetyl-5butyl-3-methyl-4,6-dioxo-octahydro-pyrrolo[3,4-c]pyrrol-1-yl)-benzimidamide;

(3 aRS,4SR,6RS,6aSR)-4-[4-(amino-hydroxyimino-methyl)-phenyl]-2-benzyl-5,6-dimethyl-tetrahydro-pyrrolo[3,4-c]pyrrole-1,3-dione;

(1RS,3SR,3aRS,6aSR)-4-(5-butyl-3-methyl-4,6-dioxo-octahydro-pyrrolo[3,4-c]pyrrol-1-yl)-benzimidamide;

(1RS,3SR,3aRS,6aSR)-4-(5-benzyl-3-isobutyl-4,6-dioxo-octahydro-pyrrolo[3,4-c]pyrrol-1-yl)-benzimidamide;

(1RS,3SR,3aRS,6aSR)-4-(5-benzyl-3-isobutyl-2-methyl-4,6-dioxo-octahydro-pyrrolo[3,4-c]pyrrol-1-yl)-benzimidamide;

(1RS,3RS,3aSR,6aRS)-[5-(benzo[1,3]dioxol-5-ylmethyl)-3-(4-carbamimidoyl-phenyl)-4,6-dioxo-octahydro-pyrrolo[3,4-c]pyrrol-1-yl]-methanesulfonic acid;

(1RS, 3RS, 3 aRS, 6aSR)-[5-(benzo[1,3]dioxol-5-ylmethyl)-3-(4-carbamimidoyl-phenyl)-4,6-dioxo-octahydro-pyrrolo[3,4-c]pyrrol-1-yl]-methanesulfonic acid;

(1RS,3SR,3aRS,6aSR)-3-(4-carbamimidoyl-phenyl)-1-(2-methyl-sulfanyl-ethyl)-4,6-dioxo-5-phenyl-octahydro-pyrrolo[3,4-c]pyrrole-1-carboxylic acid;

(1RS,3SR,3aRS,6aSR)-4-[5-(benzo[1,3]dioxol-5-ylmethyl)-3-hydroxymethyl-4,6-dioxo-octahydro-pyrrolo[3,4-c]pyrrol-1-yl]-benzimidamide;

(1RS,3RS,3aSR,6aRS)-4-[5-(benzo[1,3]dioxol-5-ylmethyl)-3-hydroxymethyl-4,6-dioxo-octahydro-pyrrolo[3,4-c]pyrrol-1-yl]-benzimidamide;

3-tert.butyl-1-(3-guanidino-propyl)-4,6-dioxo-octahydro-pyrrolo[3,4-c]pyrrole-1-carboxamide;

3-phenyl-1-(3-guanidino-propyl)-4,6-dioxo-octahydro-pyrrolo-[3,4-c]pyrrole-1-carboxamide;

3-(2-phenyl-ethyl)-1-(3-guanidino-propyl)-4,6-dioxo-octahydro-pyrrolo[3,4-c]pyrrole-1-carboxamide;

5-methyl-3-(2-phenyl-ethyl)-1-(3-guanidino-propyl)-4,6-dioxo-octahydro-pyrrolo[3,4-c]pyrrole-1-carboxamide;

5-butyl-3-(2-phenyl-ethyl)-1-(3-guanidino-propyl)-4,6-dioxo-octahydro-pyrrolo[3,4-c]pyrrole-1-carboxamide;

5-cyclohexylmethyl-3-(2-phenyl-ethyl)-1-(3-guanidino-propyl)-4,6-dioxo-octahydro-pyrrolo[3,4-c]pyrrole-1-carboxamide;

5-benzyl-3-(2-phenyl-ethyl)-1-(3-guanidino-propyl)-4,6-dioxo-octahydro-pyrrolo[3,4-c]pyrrole-1-carboxamide;

5-phenyl-3-(2-phenyl-ethyl)-1-(3-guanidino-propyl)-4,6-dioxo-octahydro-pyrrolo[3,4-c]pyrrole-1-carboxamide;

5-butyl-3,3-diphenyl-1-(3-guanidino-propyl)-4,6-dioxo-octahydro-pyrrolo[3,4-c]pyrrole-1-carboxamide;

5-butyl-3-phenyl-1-(3-guanidino-propyl)-4,6-dioxo-octahydro-pyrrolo[3,4-c]pyrrole-1-carboxamide;

5-cyclohexylmethyl-3-phenyl-1-(3-guanidino-propyl)-4,6-dioxo-octahydro-pyrrolo[3,4-c]pyrrole-1-carboxamide ;

5-benzyl-3-phenyl-1-(3-guanidino-propyl)-4,6-dioxo-octahydro-pyrrolo[3,4-c]pyrrole-1-carboxamide;

3,5-diphenyl-1-(3-guanidino-propyl)-4,6-dioxo-octahydro-pyrrolo[3,4-c]pyrrole-1-carboxamide;

5-butyl-3-tert.butyl-1-(3-guanidino-propyl)-4,6-dioxo-octahydro-pyrrolo[3,4-c]pyrrole-1-carboxamide;

5-butyl-1-(3-guanidino-propyl)-4,6-dioxo-octahydro-pyrrolo-[3,4-c]pyrrole-1-carboxamide;

1-(3-guanidino-propyl)-4,6-dioxo-octahydro-5-phenyl-pyrrolo[3,4-c]pyrrole-1-carboxamide;

5-methyl-3-(4-carbamimidoyl-phenyl)-4,6-dioxo-octahydro-pyrrolo[3,4-c]pyrrole-1-carboxylic acid;

1,5-dimethyl-3-(4-carbamimidoyl-phenyl)-4,6-dioxo-octahydro-pyrrolo[3,4-c]pyrrole-1-carboxylic acid;

5-methyl-1-(2-propyl)-3-(4-carbamimidoyl-phenyl)-4,6-dioxo-octahydro-pyrrolo[3,4-c]pyrrole-1-carboxylic acid;

1-(2-butyl)-5-methyl-3-(4-carbamimidoyl-phenyl)-4,6-dioxo-octahydro-pyrrolo[3,4-c]pyrrole-1-carboxylic acid;

5-methyl-1-(2-methylsulfanyl-ethyl)-3-(4-carbamimidoyl-phenyl)-4,6-dioxo-octahydro-pyrrolo[3,4-c]pyrrole-1-carboxylic acid;

5-butyl-3-(4-carbamimidoyl-phenyl)-4,6-dioxo-octahydro-pyrrolo[3,4-c]pyrrole-1-carboxylic acid;

5-butyl-1-methyl-3-(4-carbamimidoyl-phenyl)-4,6-dioxo-octahydro-pyrrolo[3,4-c]pyrrole-1-carboxylic acid;

5-butyl-1-(2-propyl)-3-(4-carbamimidoyl-phenyl)-4,6-dioxo-octahydro-pyrrolo[3,4-c]pyrrole-1-carboxylic acid;

5-butyl-1-(2-butyl)-3-(4-carbamimidoyl-phenyl)-4,6-dioxo-octahydro-pyrrolo[3,4-c]pyrrole-1-carboxylic acid;

5-butyl-1-(2-methylsulfanyl-ethyl)-3-(4-carbamimidoyl-phenyl)-4,6-dioxo-octahydro-pyrrolo[3,4-c]pyrrole-1-carboxylic acid;

5-cyclohexylmethyl-3-(4-carbamimidoyl-phenyl)-4,6-dioxo-octahydro-pyrrolo[3,4-c]pyrrole-1-carboxylic acid;

5-cyclohexylmethyl-1-(2-propyl)-3-(4-carbamimidoyl-phenyl)-4,6-dioxo-octahydro-pyrrolo[3,4-c]pyrrole-1-carboxylic acid;

1-(2-butyl)-5-cyclohexylmethyl-3-(4-carbamimidoyl-phenyl)-4,6-dioxo-octahydro-pyrrolo[3,4-c]pyrrole-1-carboxylic acid;

5-cyclohexylmethyl-1-(2-methylsulfanyl-ethyl)-3-(4-carbamimidoyl-phenyl)-4,6-dioxo-octahydro-pyrrolo[3,4-c]pyrrole-1-carboxylic acid;

5-phenyl-3-(4-carbamimidoyl-phenyl)-4,6-dioxo-octahydro-pyrrolo[3,4-c]pyrrole-1-carboxylic acid;

1-methyl-5-phenyl-3-(4-carbamimidoyl-phenyl)-4,6-dioxo-octahydro-pyrrolo[3,4-c]pyrrole-1-carboxylic acid;

5-phenyl-1-(2-propyl)-3-(4-carbamimidoyl-phenyl)-4,6-dioxo-octahydro-pyrrolo[3,4-c]pyrrole-1-carboxylic acid;

1-(2-butyl)-5-phenyl-3-(4-carbamimidoyl-phenyl)-4,6-dioxo-octahydro-pyrrolo[3,4-c]pyrrole-1-carboxylic acid;

1-(2-methylsulfanyl-ethyl)-5-phenyl-3-(4-carbamimidoyl-phenyl)-4,6-dioxo-octahydro-pyrrolo[3,4-c]pyrrole-1-carboxylic acid;

5-benzyl-3-(4-carbamimidoyl-phenyl)-4,6-dioxo-octahydro-pyrrolo[3,4-c]pyrrole-1-carboxylic acid;

5-benzyl-1-methyl-3-(4-carbamimidoyl-phenyl)-4,6-dioxo-octahydro-pyrrolo[3,4-c]pyrrole-1-carboxylic acid;

5-benzyl-1-(2-propyl)-3-(4-carbamimidoyl-phenyl)-4,6-dioxo-octahydro-pyrrolo[3,4-c]pyrrole-1-carboxylic acid;

5-benzyl-1-(2-butyl)-3-(4-carbamimidoyl-phenyl)-4,6-dioxo-octahydro-pyrrolo[3,4-c]pyrrole-1-carboxylic acid;

5-benzyl-3-(4-carbamimidoyl-phenyl)-1-(2-methylsulfanyl-ethyl)-4,6-dioxo-octahydro-pyrrolo[3,4-c]pyrrole-1-carboxylic acid;

5-methyl-1-(4-carbamimidoyl-phenyl)-2-(2-carbamoyl-ethyl)-4,6-dioxo-octahydro-pyrrolo[3,4-c]pyrrole-3-carboxylic acid;

3,5-dimethyl-1-(4-carbamimidoyl-phenyl)-2-(2-carbamoyl-ethyl)-4,6-dioxo-octahydro-pyrrolo[3,4-c]pyrrole-3-carboxylic acid;

5-methyl-3-(prop-2-yl)-1-(4-carbamimidoyl-phenyl)-2-(2-carbamoyl-ethyl)-4,6-dioxo-octahydro-pyrrolo[3,4-c]pyrrole-1-carboxylic acid;

5-methyl-3-(2-methyl-propyl)-1-(4-carbamimidoyl-phenyl)-2-(2-carbamoyl-ethyl)-4,6-dioxo-octahydro-pyrrolo[3,4-c]pyrrole-1-carboxylic acid;

3-hydroxymethyl-5-methyl-1-(4-carbamimidoyl-phenyl)-2-(2-carbamoyl-ethyl)-4,6-dioxo-octahydro-pyrrolo[3,4-c]pyrrole-1-carboxylic acid;

3-benzyl-5-methyl-1-(4-carbamimidoyl-phenyl)-2-(2-carbamoyl-ethyl)-4,6-dioxo-octahydro-pyrrolo[3,4-c]pyrrole-1-carboxylic acid;

5-butyl-1-(4-carbamimidoyl-phenyl)-2-(2-carbamoyl-ethyl)-4,6-dioxo-octahydro-pyrrolo[3,4-c]pyrrole-1-carboxylic acid;

5-butyl-3-methyl-1-(4-carbamimidoyl-phenyl)-2-(2-carbamoyl-ethyl)-4,6-dioxo-octahydro-pyrrolo[3,4-c]pyrrole-1-carboxylic acid;

5-butyl-3-(prop-2-yl)-1-(4-carbamimidoyl-phenyl)-2-(2-carbamoyl-ethyl)-4,6-dioxo-octahydro-pyrrolo[3,4-c]pyrrole-1-carboxylic acid;

5-butyl-3-(2-methyl-propyl)-1-(4-carbamimidoyl-phenyl)-2-(2-carbamoyl-ethyl)-4,6-dioxo-octahydro-pyrrolo[3,4-c]pyrrole-1-carboxylic acid;

5-butyl-3-hydroxymethyl-1-(4-carbamimidoyl-phenyl)-2-(2-carbamoyl-ethyl)-4,6-dioxo-octahydro-pyrrolo[3,4-c]pyrrole-1-carboxylic acid;

3-benzyl-5-butyl-1-(4-carbamimidoyl-phenyl)-2-(2-carbamoyl-ethyl)-4,6-dioxo-octahydro-pyrrolo[3,4-c]pyrrole-1-carboxylic acid;

3-methyl-5-phenyl-1-(4-carbamimidoyl-phenyl)-2-(2-carbamoyl-ethyl)-4,6-dioxo-octahydro-pyrrolo[3,4-c]pyrrole-1-carboxylic acid;

5-phenyl-3-(prop-2-yl)-1-(4-carbamimidoyl-phenyl)-2-(2-carbamoyl-ethyl)-4,6-dioxo-octahydro-pyrrolo[3,4-c]pyrrole-1-carboxylic acid;

3-(2-methyl-propyl)-5-phenyl-1-(4-carbamimidoyl-phenyl)-2-(2-carbamoyl-ethyl)-4,6-dioxo-octahydro-pyrrolo[3,4-c]pyrrole-1-carboxylic acid;

3-hydroxymethyl-5-phenyl-1-(4-carbamimidoyl-phenyl)-2-(2-carbamoyl-ethyl)-4,6-dioxo-octahydro-pyrrolo[3,4-c]pyrrole-1-carboxylic acid;

3-benzyl-5-phenyl-1-(4-carbamimidoyl-phenyl)-2-(2-carbamoyl-ethyl)-4,6-dioxo-octahydro-pyrrolo[3,4-c]pyrrole-1-carboxylic acid;

5-benzyl-3-methyl-1-(4-carbamimidoyl-phenyl)-2-(2-carbamoyl-ethyl)-4,6-dioxo-octahydro-pyrrolo[3,4-c]pyrrole-1-carboxylic acid;

5-benzyl-3-(2-methyl-propyl)-1-(4-carbamimidoyl-phenyl)-2-(2-carbamoyl-ethyl)-4,6-dioxo-octahydro-pyrrolo[3,4-c]pyrrole-1-carboxylic acid;

5-benzyl-3-hydroxymethyl-1-(4-carbamimidoyl-phenyl)-2-(2-carbamoyl-ethyl)-4,6-dioxo-octahydro-pyrrolo[3,4-c]pyrrole-1-carboxylic acid;

3,5-dibenzyl-1-(4-carbamimidoyl-phenyl)-2-(2-carbamoyl-ethyl)-4,6-dioxo-octahydro-pyrrolo[3,4-c]pyrrole-1-carboxylic acid;

5-(2-phenyl-ethyl)-1-(4-carbamimidoyl-phenyl)-2-(2-carbamoyl-ethyl)-4,6-dioxo-octahydro-pyrrolo[3,4-c]pyrrole-1-carboxylic acid;

5-(2-phenyl-ethyl)-3-(prop-2-yl)-1-(4-carbamimidoyl-phenyl)-2-(2-carbamoyl-ethyl)-4,6-dioxo-octahydro-pyrrolo[3,4-c]pyrrole-1-carboxylic acid;

3-(2-methyl-propyl)-5-(2-phenyl-ethyl)-1-(4-carbamimidoyl-phenyl)-2-(2-carbamoyl-ethyl)-4,6-dioxo-octahydro-pyrrolo[3,4-c]pyrrole-1-carboxylic acid;

3-hydroxymethyl-5-(2-phenyl-ethyl)-1-(4-carbamimidoyl-phenyl)-2-(2-carbamoyl-ethyl)-4,6-dioxo-octahydro-pyrrolo[3,4-c]pyrrole-1-carboxylic acid;

3-benzyl-1-(4-carbamimidoyl-phenyl)-2-(2-carbamoyl-ethyl)-4,6-dioxo-octahydro-5-(2-phenyl-ethyl)-pyrrolo[3,4-c]pyrrole-3-carboxylic acid;

(1RS,3RS,3aSR,6aRS)-4-[3-(benzyloxy-methyl)-5-(4-nitro-benzyl)-4,6-dioxo-octahydro-pyrrolo[3,4-c]pyrrol-1-yl]-benzimidamide; and (1RS,3RS,3aSR,6aRS)-4-[5-(4-amino-benzyl)-3-(benzyloxy-methyl)-4,6-dioxo-octahydro-pyrrolo[3,4-c]pyrrol-1-yl]-benzimidamide.

16. The compound of claim 4, wherein one methylene group is substituted with lower-alkenyl and another methylene group is substituted with lower-alkyl-COOH.

17. The compound of claim 4, wherein a methylene group of group G is replaced by S, CH-lower-alkyl or CHOH.

18. The compound of claim 4, wherein G is selected from the group consisting of $(CH_2)_3$, $(CH_2)_4$, $CH(CH_3)CH_2CH_2$, $CH_2SCH_2$, $CH_2S(O)_2CH_2$, $CH_2CH(OH)CH_2$ and $CH(CH_2COOH)CH(isopropylene)CH_2$.

19. The compound of claim 4, wherein $R^1$ is selected from the group consisting of H; lower alkyl; aryl; and lower-aryl substituted with $CONH_2$ or COO-lower-alkyl, aryl or cycloalkyl.

20. The compound of claim 19, wherein $R^1$ is selected from the group consisting of $CH_3$; benzyl; benzyl substituted with methylenedioxy; butyl; phenyl; cyclohexylmethyl; lower-alkyl substituted with $CONH_2$ or with COO-lower-alkyl and aryl.

21. The compound of claim 20, wherein $R^1$ is selected from the group consisting of benzo[1,3]dioxol-5-ylmethyl and 1-(carbamoyl or carbomethoxy)-2-phenethyl.

22. The compound of claim 21, wherein $R^3$ is H or COOH.

23. The compound of claim 22, wherein $R^5$ is H.

24. The compound of claim 22, wherein $R^6$ is aryl or heteroaryl.

25. The compound of claim 24, wherein $R^6$ is selected from the group consisting of amidinophenyl, guanidinophenyl and diaminoquinazoline.

26. The compound of claim 22 selected from the group consisting of:

(3aRS,4SR,8aRS,8bSR)-4-(2-Benzyl-1,3-dioxo-decahydro-pyrrolo[3,4-a]pyrrolizin-4-yl)-benzimidamide;

(3aRS,4SR, 8aRS,8bSR)-4-[2-(benzo[1,3]dioxol-5-ylmethyl)-1,3-dioxo -decahydro-pyrrolo[3,4-a]pyrrolizin-4-yl]-benzimidamide;

(3aRS,4SR,8aRS,8bSR)-4-(2-cyclohexylmethyl-1,3-dioxo-decahydro-pyrrolo[3,4-a]pyrrolizin-4-yl)-benzimidamide;

(5RS,5aSR,5aRS,8bRS)-4-[7-(benzo[1,3]dioxol-5-ylmethyl)-6,8-dioxo-octahydro -pyrrolo[3',4':3,4]pyrrolo[1,2-c]thiazol-5-yl]- benzimidamide;

(3aR,4S,7S,8aR,8bS)-4-(2-benzyl-7-hydroxy-1,3-dioxo-decahydro-pyrrolo[3,4-a]pyrrolizin-4-yl)-benzimidamide; and (3 aRS,4S R, 8 aRS, 8 bS R)- N-[4-(2-butyl-1,3-dioxo-decahydro-pyrrolo[3,4-a]pyrrolizin-4-yl)-phenyl]-guanidine.

27. The compound of claim 22 selected from the group consisting of:

(3aRS,4SR,8aRS,8bSR)-4-(2-Butyl-1,3-dioxo-decahydro-pyrrolo[3,4-a]pyrrolizin-4-yl)-benzimidamide;

(3aRS,4RS,9aSR,9bSR)-4-(2-benzyl-1,3-dioxo-decahydro-pyrrolo[3,4-c]indolizin-4-yl)-benzimidamide;

(3aRS,4S R,9aRS,9bSR)-4-(2-benzyl-1,3-dioxo-decahydro-pyrrolo[3,4-c]indolizin-4-yl)-benzimidamide;

(3aRS,4RS,8aSR,8bSR)-4-[2-(benzo[1,3]dioxol-5-ylmethyl)-1,3-dioxo-decahydro -pyrrolo[3,4-a]pyrrolizin-4-yl]-benzimidamide;

(5RS,5aRS,8aSR,8bRS)-4-[7-(benzo[1,3]dioxol-5-ylmethyl)-6,8-dioxo-octahydro -pyrrolo[3',4':3,4]pyrrolo[1,2-c]thiazol-5-yl]-benzimidamide;

(3aS,4R,8S,8aS,8bR)-4-[2-(benzo[1,3]dioxol-5-ylmethyl)-8-methyl-1,3-dioxo-decahydro-pyrrolo[3,4-a]pyrrolizin-4-yl]-benzimidamide;

(3aR,4R,7R,8aS,8bS)-4-(2-benzyl-7-hydroxy-1,3-dioxo-decahydro-pyrrolo[3,4-a]pyrrolizin-4-yl)-benzimidamide;

methyl (R)-2-[(3aS,4S,8aR,8bR)- and -(3aR,4R,8aS,8bS) -4-(4-carbamimidoyl-phenyl)-1,3-dioxo-decahydro-pyrrolo[3,4-a]-pyrrolizin-2-yl]-3-phenyl-propionate;

methyl (R)-2-[(3aR,4S,8aR,8bS) and -(3aS,4R,8aR,8bR) -4-(4-carbamimidoyl-phenyl)-1,3-dioxo-decahydro-pyrrolo[3,4-a]-pyrrolizin-2-yl]-3-phenyl-propionate;

(1S,2S,SR,5aS,8aR)-[7-benzyl-5-(4-carbamimidoyl-phenyl)-2-(propen-2-yl)-6,8-dioxo-decahydro-pyrrolo [3,4-a]pyrrolizin-1-yl]-acetic acid;

(5RS,5aSR,8aRS,8bRS)-4-[7-(benzo[1,3]dioxol-5-ylmethyl)-2,2,6,8-tetraoxo-octahydro-pyrrolo[3',4':3,4]pyrrolo[1,2-c]thiazol-5-yl]-benzimidamide;

(3aRS,4S R, 8aRS, 8 bSR)-N-[4-(2-benzyl-1,3-dioxo-decahydro-pyrrolo[3,4-a]pyrrolizin-4-yl)-phenyl]-guanidine;

(3aRS,4SR,8aRS,8bSR)-N-[4-[2-(benzo[1,3]dioxol-5-ylmethyl)-1,3-dioxo-decahydro-pyrrolo[3,4-a]pyrrolizin-4-yl]-phenyl]-guanidine;

(3aRS,4SR,8aRS,8bSR)-2-benzyl-4-(2,4-diaminoquinazolin-6-yl)-hexahydro-pyrrolo[3,4-a]pyrrolizine-1,3-dione;

(3aRS,4RS,8aSR,8bSR)-2-benzyl-4-(2,4-diaminoquinazolin-6-yl)-hexahydro-pyrrolo[3,4-a]pyrrolizine-1,3-dione;

(3aRS,4SR,8aRS,8bSR)-2-benzyl-4-(2,4-diaminoquinazolin-7-yl)-hexahydro-pyrrolo[3,4-a]pyrrolizine-1,3-dione;

[2-methyl-4-(4-carbamimidoyl-phenyl)-1,3-dioxo-decahydro-pyrrolo[3,4-a]pyrrolizin-8a-yl]-carboxylic acid;

[2-butyl-4-(4-carbamimidoyl-phenyl)-1,3-dioxo-decahydro-pyrrolo[3,4-a]pyrrolizin-8a-yl]-carboxylic acid;

[2-cyclohexylmethyl-4-(4-carbamimidoyl-phenyl)-1,3-dioxo-decahydro-pyrrolo[3,4-a]pyrrolizin-8a-yl]-carboxylic acid;

[2-phenyl-4-(4-carbamimidoyl-phenyl)-1,3-dioxo-decahydro-pyrrolo[3,4-a]pyrrolizin-8a-yl]-carboxylic acid;

[2-benzyl-4-(4-carbamimidoyl-phenyl)-1,3-dioxo-decahydro-pyrrolo[3,4-a]pyrrolizin-8a-yl]-carboxylic acid; and 2-[4-(4-carbamimidoyl-phenyl)-1,3-dioxo-decahydro-pyrrolo[3,4-a]pyrrolizin-2-yl]-3-phenyl-propionamide.

28. A method of inhibiting thrombin-induced or Factor Xa-induced platelet aggregation and fibrinogen clotting in blood plasma comprising administering to a host a composition containing an effect amount of the compound of claim 1.

29. A pharmaceutical composition comprising at least one compound of Formula I, claim 1.

30. A method for the therapy of thrombosis, comprising the administration to a patient of an effective amount of a compound of Formula I, claim 1.

31. The method of claim 30, wherein the effective amount is from about 0.1 mg/kg to about 20 mg/kg per day.

* * * * *

UNITED STATES PATENT AND TRADEMARK OFFICE
CERTIFICATE OF CORRECTION

PATENT NO. : 5,686,459
DATED : November 11, 1997
INVENTOR(S) : Francois Diederich, et. al.

It is certified that error appears in the above-identified patent and that said Letters Patent is hereby corrected as shown below:

In claim 26, column 35, line 18, delete "(5RS,5aSR,5aRS,8bRS)-4-[7-(benzo[1,3]dioxol-5-" and insert -- (5RS,5aSR,8aRS,8bRS)-4-[7-(benzo[1,3]dioxol-5- --.

In claim 27, column 36, line 1, delete "(1S,2S,SR,5aS,8aR)-[7-benzyl-5-(4-carbamimidoyl-" and insert -- (1S,2S,5R,5aS,8aR)-[7-benzyl-5-(4-carbamimidoyl- --.

Signed and Sealed this

Tenth Day of March, 1998

Attest:

BRUCE LEHMAN

*Attesting Officer*  *Commissioner of Patents and Trademarks*